United States Patent
Chung et al.

(10) Patent No.: US 11,767,292 B2
(45) Date of Patent: *Sep. 26, 2023

(54) PROCESS FOR MAKING BETA 3 AGONISTS AND INTERMEDIATES

(71) Applicant: Merck Sharp & Dohme Corp., Rahway, NJ (US)

(72) Inventors: John Y. L. Chung, Edison, NJ (US); Kevin Campos, Berkeley Heights, NJ (US); Edward Cleator, Cambridge (GB); Robert F. Dunn, Towaco, NJ (US); Andrew Gibson, Hoddesdon (GB); R. Scott Hoerrner, Westfield, NJ (US); Stephen Keen, Hoddesdon (GB); Dave Lieberman, Hoddesdon (GB); Zhuqing Liu, Edison, NJ (US); Joseph Lynch, Plainfield, NJ (US); Kevin M. Maloney, Piscataway, NJ (US); Feng Xu, Staten Island, NY (US); Nobuyoshi Yasuda, Mountainside, NJ (US); Naoki Yoshikawa, Hyogo (JP); Yong-Li Zhong, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 63 days.

This patent is subject to a terminal disclaimer.

(21) Appl. No.: 17/478,601

(22) Filed: Sep. 17, 2021

(65) Prior Publication Data
US 2022/0073459 A1    Mar. 10, 2022

Related U.S. Application Data

(60) Continuation of application No. 16/795,745, filed on Feb. 20, 2020, now Pat. No. 11,124,478, which is a division of application No. 15/715,493, filed on Sep. 26, 2017, now Pat. No. 10,577,316, which is a continuation of application No. 14/354,161, filed as application No. PCT/US2012/061249 on Oct. 22, 2012, now Pat. No. 9,809,536.

(60) Provisional application No. 61/552,200, filed on Oct. 27, 2011.

(51) Int. Cl.
C07D 207/09    (2006.01)
C07D 207/08    (2006.01)
C12P 17/10    (2006.01)

(52) U.S. Cl.
CPC ......... C07D 207/09 (2013.01); C07D 207/08 (2013.01); C12P 17/10 (2013.01)

(58) Field of Classification Search
CPC ...... C07D 207/09; C07D 207/08; C12P 17/10
See application file for complete search history.

(56) References Cited

U.S. PATENT DOCUMENTS

| | | |
|---|---|---|
| 6,525,202 B2 | 2/2003 | Hu et al. |
| 7,396,958 B2 | 7/2008 | Courtemanche et al. |
| 8,247,415 B2 | 8/2012 | Berger et al. |
| 8,399,480 B2 | 3/2013 | Berger et al. |
| 8,415,126 B2 | 4/2013 | Mundorff et al. |
| 8,653,260 B2 | 2/2014 | Berger et al. |
| 8,748,143 B2 | 6/2014 | Liang et al. |
| 8,748,433 B2 | 6/2014 | Berger et al. |
| 9,809,536 B2 | 11/2017 | Chung et al. |
| 9,822,121 B2 | 11/2017 | Chung et al. |
| 10,087,189 B2 | 10/2018 | Chung et al. |
| 10,287,289 B2 | 5/2019 | Xu et al. |
| 10,435,410 B2 | 10/2019 | Chung et al. |
| 10,696,681 B2 | 6/2020 | Chapman et al. |
| 10,899,771 B2 | 1/2021 | Chung et al. |
| 11,091,493 B2 | 8/2021 | Xu et al. |
| 2011/0028481 A1* | 2/2011 | Berger ............... C07D 403/12 548/194 |
| 2012/0202819 A1 | 8/2012 | Edmondson et al. |
| 2015/0087832 A1 | 3/2015 | Chung et al. |
| 2021/0221815 A1 | 7/2021 | Chung et al. |
| 2022/0073523 A1 | 3/2022 | Xu et al. |

FOREIGN PATENT DOCUMENTS

| | | |
|---|---|---|
| WO | WO 03/072572 A1 | 9/2003 |
| WO | WO 2009/124166 A1 | 10/2009 |
| WO | WO 2009/124167 A1 | 10/2009 |
| WO | WO 2011/043942 A1 | 4/2011 |
| WO | WO 2013/062878 A1 | 5/2013 |

(Continued)

OTHER PUBLICATIONS

International Search Report for U.S. Application No. PCT/US2012061249, United States Patent Office, United States, dated Dec. 28, 2012.

(Continued)

*Primary Examiner* — Paul J Holland

(57) ABSTRACT

The present invention is directed to a process for preparing a compound of formula I-11 through multiple-step reactions:

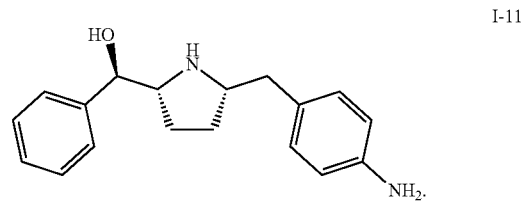

I-11

12 Claims, No Drawings

Specification includes a Sequence Listing.

(56) References Cited

FOREIGN PATENT DOCUMENTS

| WO | WO 2013/062881 A1 | 5/2013 |
|---|---|---|
| WO | WO 2013/074650 A1 | 5/2013 |
| WO | WO 2014/150639 A1 | 9/2014 |

OTHER PUBLICATIONS

Adkins H et al. The preparation of Raney Nickel catalysts and their use under conditions comparable with those for platinum and palladium catalysts. 1948. Contribution from the Laboratory of Organic Chemistry, University of Wisconsin. 695-698.
Hultin PG. A Guide to Solvents and Reagents in Introductory Organic Chemistry for students in 2.222. 2002. p. 1-20.
Morriello, Design of a novel pyrrolidine scaffold utilized in the discovery of potent and selective human beta 3adrenergic receptor agonists, Bioorganic & Medicinal Chemistry Letters, 2011, 1865-1870, 21 (6).
Extended European Search Report for 12842776.2, dated Mar. 12, 2015; 4 pages.
Dong, S., et al., "Convenient syntheses of homopropargylglycine," *Journal of Peptide Science* 74:1148-1150, John Wiley & Sons, Ltd., England (2008).
Haynes, W.M., "Dissociation Constants of Organic Acids and Bases," in *CRC Handbook of Chemistry and Physics*, 92$^{nd}$ Edition, Haynes, W.M., et al., eds., Section 5, pp. 94-103, Taylor & Francis Group, United States (2011).
Huisman, G.W., et al., "Practical chiral alcohol manufacture using ketoreductases," *Current Opinion in Chemical Biology* 74:122-129, Elsevier Ltd., England (2010).
Kaiser, H-P. and Muchowski, J.M., "Catalytic Hydrogenation of Pyrroles at Atmospheric Pressure," *Journal of Organic Chemistry* 490:4203-4209, American Chemical Society, United States (1984).
Wuts, P.G.M., "The Role of Protective Groups in Organic Synthesis," in *Greene's Protective Groups in Organic Synthesis*, Fourth Edition, Wuts, P.G.M. and Greene, T.W., eds., Chapter 1, pp. 1-15, John Wiley & Sons, Inc., United States (2007).
Xu, F., et al., "Asymmetric Synthesis of cis-2,5-Disubstituted Pyrrolidine, the Core Scaffold of $\beta_3$-AR Agonists," *Organic Letters* 15(6):1342-1345, American Chemical Society, United States (2013).
International Preliminary Report on Patentability and Written Opinion for International Application No. PCT/US2009/039249, The International Bureau of WIPO, Geneva, Switzerland, dated Oct. 5, 2010, 6 pages.
International Preliminary Report on Patentability and Written Opinion for International Application No. PCT/US2009/039253 The International Bureau of WIPO, Geneva, Switzerland, dated Oct. 5, 2010, 5 pages.
International Preliminary Report on Patentability and Written Opinion for International Application No. PCT/US2014/023858, The International Bureau of WIPO, Geneva, Switzerland, dated Sep. 15, 2015, 5 pages.
International Preliminary Report on Patentability and Written Opinion for International Application No. PCT/US2012/061252, The International Bureau of WIPO, Geneva, Switzerland, dated Apr. 29, 2014, 4 pages.
International Search Report for International Application No. PCT/US2009/039249, European Patent Office, Netherlands, dated Aug. 31, 2009, 4 pages.
International Search Report for International Application No. PCT/US2009/039253, European Patent Office, Netherlands, dated Jun. 17, 2009, 3 pages.
International Search Report for International Application No. PCT/US2014/023858, European Patent Office, Netherlands, dated Jun. 6, 2014, 3 pages.
International Search Report for International Application No. PCT/US2012/061252, European Patent Office, Netherlands, dated Jan. 18, 2013, 2 pages.
Devos, D. and Valencia, A., "Practical limits of function prediction," *Proteins: Structure, Function, and Genetics* 41:98-107, Wiley-Liss, Inc., United States (2000).
Kisselev, L., "Polypeptide Release Factors in Prokaryotes and Eukaryotes: Same Function, Different Structure," *Structure* 10(1):8-9, Elsevier Science Ltd., England (2002).
Whisstock, J.C. and Lesk, A.M., "Prediction of protein function from protein sequence and structure," *Quarterly Reviews of Biophysics* 36(3):307-340, Cambridge University Press, United Kingdom (2003).
Witkowski, A., et al., "Conversion of a β-Ketoacyl Synthase to a Malonyl Decarboxylase by Replacement of the Active-Site Cysteine with Glutamine," *Biochemistry* 38(36):11643-11650, American Chemical Society, United States (1999).
Office Action dated Aug. 17, 2017, in U.S. Appl. No. 14/776,366, Xu, F. et al., § 371(c) date Sep. 14, 2015, 15 pages.
International Preliminary Report on Patentability and Written Opinion for International Application No. PCT/US2012/061249, The International Bureau of WIPO, Geneva, Switzerland, dated Apr. 29, 2014, 4 pages.
Office Action dated Dec. 10, 2020, in U.S. Appl. No. 16/914,138, Xu, F. et al., filed Jun. 26, 2020, 7 pages.
Office Action dated Aug. 18, 2022, in U.S. Appl. No. 17/399,274 Xu, F. et al., filed Aug. 18, 2022, 6 pages.
Office Action dated Feb. 7, 2019, in U.S. Appl. No. 16/133,320, Chung, J. Y.L. et al., filed Sep. 17, 2018, 5 pages.
Office Action dated Jun. 2, 2020, in U.S. Appl. No. 16/590,180, Chung, J. Y.L. et al., filed Oct. 1, 2019, 8 pages.
Office Action dated Aug. 16, 2022, in U.S. Appl. No. 17/155,982, Chung, J. Y.L. et al., filed Jan. 23, 2021, 9 pages.

\* cited by examiner

PROCESS FOR MAKING BETA 3 AGONISTS AND INTERMEDIATES

TECHNICAL FIELD

The present disclosure relates to a process for making beta 3 agonists and intermediates, ketoreductase (KRED) biocatalysts and methods of using the biocatalysts.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of 3987_0050004_SeqListing.txt, a creation date of Sep. 17, 2021, and a size of 10,017 bytes. The Sequence Listing filed via EFS-Web is part of the specification and is incorporated in its entirety by reference herein.

BACKGROUND OF THE INVENTION

This application is directed to an efficient and economical synthetic process for making a compound of formula I-11 which can be used as an intermediate compound for making beta 3 agonists.

SUMMARY OF THE INVENTION

This application is directed to a multiple-step synthetic process for making a compound of formula I-11. In one embodiment, a KRED enzyme is used in the multiple-step process.

DESCRIPTION OF THE INVENTION

Described herein is a process of making compound I-11 from compound I-1 through multiple step reactions:

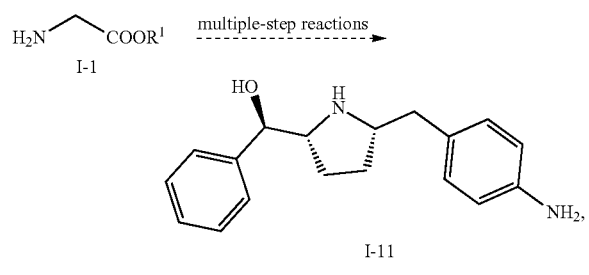

wherein $R^1$ is selected from the group consisting of $C_{1-6}$ alkyl, benzyl and phenyl.

In one embodiment, the multiple-step reactions from compound I-1 to compound I-11 comprise the following steps:

(a) reacting compound I-4:

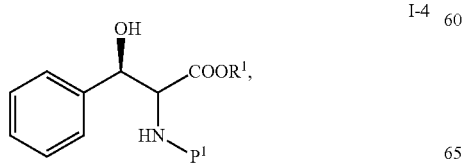

with an acetonide protection reagent selected from the group consisting of 2,2-dimethoxy propane, 2,2-diethoxylpropane, 2-methoxypropene and acetone, to produce compound I-5:

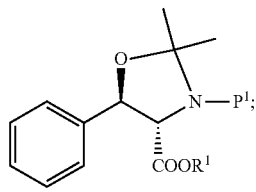

(b) reducing compound I-5 with a reducing agent at a temperature of 0° C. to 40° C. to produce compound I-6:

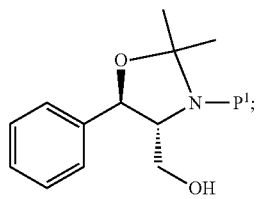

(c) oxidizing compound I-6 with an oxidizing agent in the presence of a solvent and a catalyst to produce compound I-7:

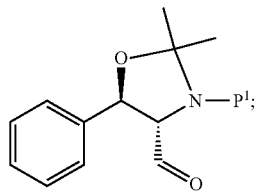

(d) reacting compound I-7 with phosphate compound A-4:

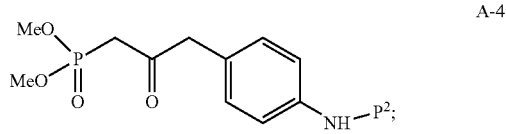

to produce compound I-8:

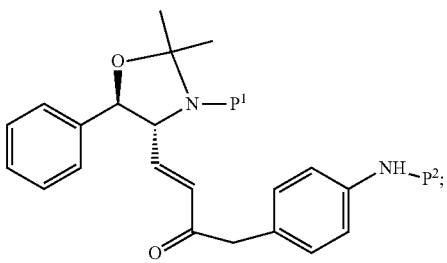

(e) reducing compound I-8 in the presence of a catalyst to produce compound I-9:

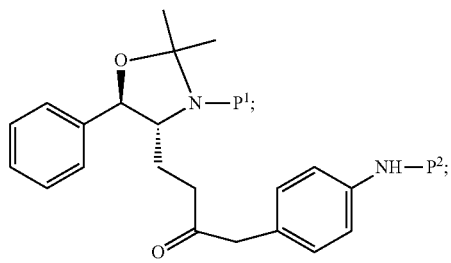

(f) reacting compound I-9 with an acid to produce compound I-10:

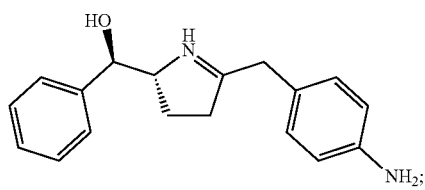

and (g) reducing compound I-10 in the presence of a catalyst to produce compound I-11;

wherein $P^1$ and $P^2$ are each independently selected from the group consisting of Ac, Bn, Boc, Bz, Cbz, DMPM, FMOC, Ns, Moz, and Ts; and $R^1$ is selected from the group consisting of $C_{1-6}$alkyl, benzyl and phenyl.

In one embodiment, the solvent in step (c) above is selected from the group consisting of THF, MTBE, $CH_2Cl_2$, MeCN, toluene and a mixture comprising two of the foregoing solvents. In another embodiment, the oxidizing agent is selected from the group consisting of NaOCl, $NaClO_2$, hydrogen peroxide, pyridine sulfur trioxide, PCC, and DCC. In another embodiment, the catalyst is TEMPO or a TEMPO analogue.

In one embodiment, the reaction between I-7 and A-4 in step (d) is carried out at a temperature of about 20 to 40° C. In another embodiment, the reaction is carried out in the presence of a solvent selected from the group consisting of THF, MTBE, $CH_2Cl_2$, MeCN, toluene and a mixture comprising two of the foregoing solvents.

In one embodiment, the catalyst used in the reduction step (e) is selected from the group consisting of Pd, Raney Ni, Pt, $PdCl_2$, and $Pd(OH)_2$. In another embodiment, the reduction is carried out in the presence of hydrogen gas.

In one embodiment, the acid in step (f) is selected from the group consisting of HCl, HBr, TFA, $MeSO_3H$, TfOH, $H_2SO_4$, para-toluenesulfonic acid, and $RSO_3H$ wherein R is alkyl, aryl or substituted aryl.

In one embodiment, the reduction of step (g) is carried out in the presence of HMDS. In another embodiment, the catalyst used is selected from the group consisting of Pt on alumina, Pd on alumina, Pd/C, $Pd(OH)_2$—C, Raney Ni, Rh/C, Rh/Al, Pt/C, Ru/C and $PtO_2$.

In one embodiment, the multiple-step reactions from compound I-1 to compound I-11 further comprise reducing compound I-3:

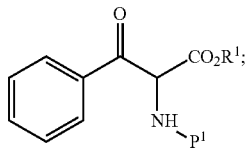

in the presence of a KRED enzyme to produce compound I-4:

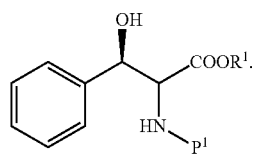

In one embodiment, the KRED enzyme is selected from the group consisting of a polypeptide of SEQ ID NO. 1 and a polypeptide of SEQ ID NO. 2.

In another embodiment, a cofactor recycling system is also present in addition to a KRED enzyme. Suitable cofactor recycling systems include, but are not limited to, a polypeptide of SEQ ID NO. 3 and a polypeptide of SEQ ID NO. 4.

In one embodiment, a KRED enzyme of SEQ ID NO. 1 and a cofactor recycling system of SEQ ID NO. 3 are present in the reduction from I-3 to I-4.

In another embodiment, a KRED enzyme of SEQ ID NO. 2 and a cofactor recycling system of SEQ ID NO. 4 are present in the reduction from I-3 to I-4.

In one embodiment, a cofactor molecule which can donate an electron is also present in addition to a KRED enzyme. In one embodiment, the cofactor is selected from the group consisting of NADH and NADPH.

In one embodiment, the multiple-step reactions from compound I-1 to compound I-11 further comprise reacting compound I-1:

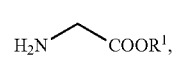

with benzoyl chloride and a protecting reagent to produce compound I-3:

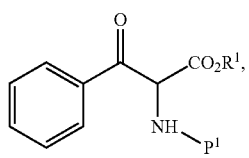

wherein $P^1$ is a protecting group selected from the group consisting of Ac, Bn, Boc, Bz, Cbz, DMPM, FMOC, Moz, and Ts; and $R^1$ is $C_{1-6}$alkyl or an aryl.

In one embodiment, $R^1$ is methyl, ethyl, propyl or butyl. In another embodiment, $R^1$ is methyl, ethyl, or phenyl. In one embodiment, $P^1$ is Boc.

In one embodiment, the conversion from compound I-1 to compound I-3 is carried out through compound I-2:

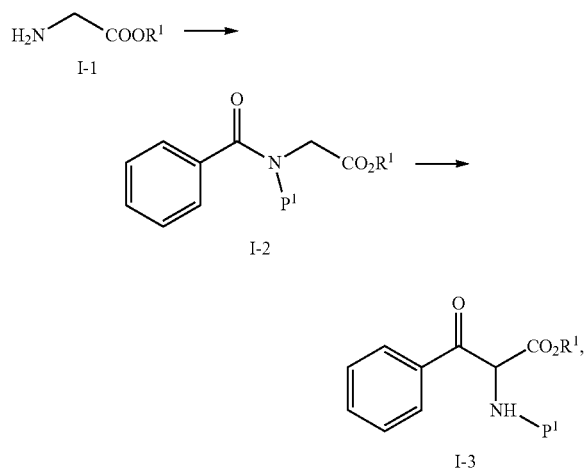

wherein $R^1$ is $C_{1-6}$alkyl or an aryl; and $P^1$ is selected from the group consisting of Ac, Bn, Boc, Bz, Cbz, DMPM, FMOC, Moz, and Ts.

In one embodiment, the conversion from I-1 to I-3 comprises:

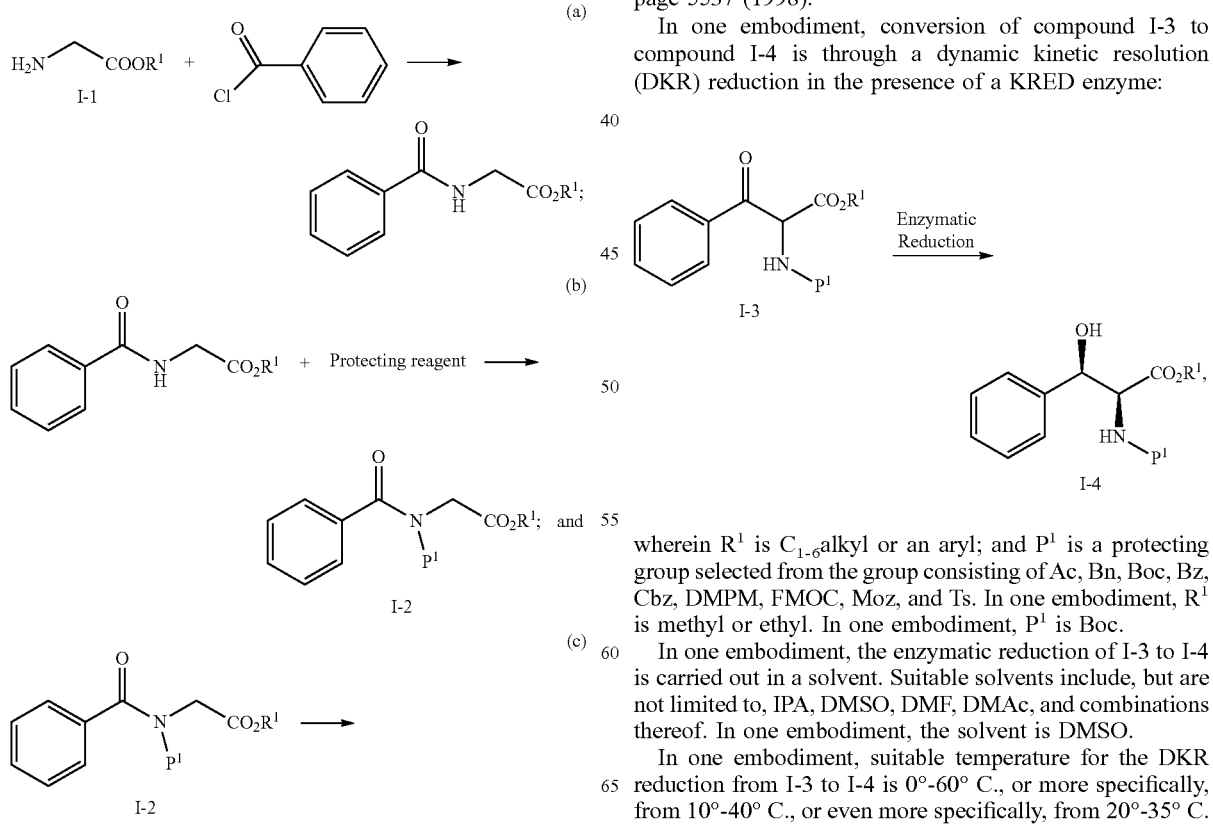

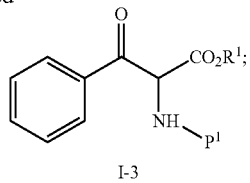

wherein $R^1$ is $C_{1-6}$alkyl or an aryl; and $P^1$ is selected from the group consisting of Ac, Bn, Boc, Bz, Cbz, DMPM, FMOC, Moz, and Ts. In one embodiment, $R^1$ is methyl or ethyl and $P^1$ is Boc.

In one embodiment, step (a) or (b) above is carried out in the presence of a base. Suitable bases include, but are not limited to, NaOH, KOH, $Na_2CO_3$, $K_2CO_3$, $NaHCO_3$, $K_3PO_4$, $Et_3N$, i-$Pr_2Net$, and pyridine. In one embodiment, the base is $NaHCO_3$, $Na_2CO_3$ or $Et_3N$.

In one embodiment, the protecting reagent in step (b) is $Boc_2O$.

In one embodiment, the conversion from I-1 to I-3 is carried out in the presence of a suitable catalyst. In one embodiment, the catalyst is DMAP.

In one embodiment, the conversion from I-1 to I-3 is carried out at a temperature of 0° C. to 60° C., or more specifically, 0° C. to 40° C., or even more specifically, 20° C. to 30° C. In one embodiment, the temperature is 20° C. to 30° C.

In one embodiment, the above conversion from I-1 to I-3 can be carried out using similar synthetic processes as described in Novel N→C Acyl Migration Reaction of Acyclic Imides: A Facile Method for α-Aminoketones and β-Aminoalcohols, Hara, et. al., Tetrahedron Letter, Vol. 39, page 5537 (1998).

In one embodiment, conversion of compound I-3 to compound I-4 is through a dynamic kinetic resolution (DKR) reduction in the presence of a KRED enzyme:

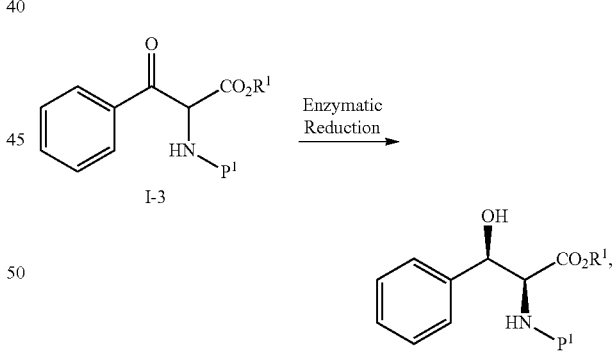

wherein $R^1$ is $C_{1-6}$alkyl or an aryl; and $P^1$ is a protecting group selected from the group consisting of Ac, Bn, Boc, Bz, Cbz, DMPM, FMOC, Moz, and Ts. In one embodiment, $R^1$ is methyl or ethyl. In one embodiment, $P^1$ is Boc.

In one embodiment, the enzymatic reduction of I-3 to I-4 is carried out in a solvent. Suitable solvents include, but are not limited to, IPA, DMSO, DMF, DMAc, and combinations thereof. In one embodiment, the solvent is DMSO.

In one embodiment, suitable temperature for the DKR reduction from I-3 to I-4 is 0°-60° C., or more specifically, from 10°-40° C., or even more specifically, from 20°-35° C. In one embodiment, the temperature is about 30° C.

In one embodiment, a KRED enzyme coupled with a cofactor recycling system and an NADPH cofactor is used to reduce compound I-3 to obtain compound I-4. Suitable reaction conditions for the KRED-catalyzed reduction of I-3 to I-4 are provided below and in the Examples.

KRED enzymes belonging to class EC1.1.1.184 are useful for the synthesis of optically active alcohols from the corresponding pro-stereoisomeric ketone substrates and by stereospecific reduction of corresponding racemic aldehyde and ketone substrates.

KRED enzymes typically convert a ketone or aldehyde substrate to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED typically require a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP+) for the oxidation reaction. NADH and NADPH serve as electron donors, while NAD and NADP serve as electron acceptors. KRED enzymes often can use either the phosphorylated or the non-phosphorylated co-factor.

KRED enzymes can be used in place of chemical procedures for the conversion of different keto and aldehyde compounds to chiral alcohol products. These biocatalytic conversions can employ whole cells expressing the ketoreductase for biocatalytic ketone reductions, or purified enzymes, particularly in those instances where presence of multiple ketoreductases in whole cells would adversely affect the enantiomeric purity and yield of the desired product. For in vitro applications, a co-factor (NADH or NADPH) regenerating enzyme such as glucose dehydrogenase (GDH) and formate dehydrogenase typically is used in conjunction with the ketoreductase.

Examples illustrating the use of naturally occurring or engineered KRED enzymes in biocatalytic processes to generate useful chemical compounds include asymmetric reduction of 4-chloroacetoacetate esters (Zhou, J. Am. Chem. Soc. 1983 105:5925-5926; Santaniello, J. Chem. Res. (S) 1984:132-133; U.S. Pat. Nos. 5,559,030; 5,700,670 and 5,891,685), reduction of dioxocarboxylic acids (e.g., U.S. Pat. No. 6,399,339), reduction of tert-butyl (S)-chloro-5-hydroxy-3-oxohexanoate (e.g., U.S. Pat. No. 6,645,746 and WO 01/40450), reduction pyrrolotriazine-based compounds (e.g., U.S. application No. 2006/0286646); reduction of substituted acetophenones (e.g., U.S. Pat. No. 6,800,477); and reduction of ketothiolanes (WO 2005/054491).

Naturally occurring KRED enzymes can be found in a wide range of bacteria and yeasts (for reviews: Kraus and Waldman, Enzyme catalysis in organic synthesis Vols. 1&2.VCH Weinheim 1995; Faber, K., Biotransformations in organic chemistry, 4th Ed. Springer, Berlin Heidelberg New York. 2000; Hummel and Kula Eur. J. Biochem. 1989 184:1-13). Several KRED gene and enzyme sequences have been reported, including: *Candida magnoliae* (Genbank Acc. No. JC7338; GI:11360538); *Candida parapsilosis* (Genbank Acc. No. BAA24528.1; GI:2815409), *Sporobolomyces salmonicolor* (Genbank Acc. No. AF160799; GI:6539734); *Lactobacillus kefir* (Genbank Acc. No. AAP94029.1; GI: 33112056); *Lactobacillus brevis* (Genbank Acc. No. 1NXQ_A; GI: 30749782); *Exiguobacterium acetylicum* (Genbank Acc. No. BAD32703.1) and *Thermoanaerobium brockii* (Genbank Acc. No. P14941; GI: 1771790).

The KRED catalyzed reduction of I-3 to I-4 requires that an electron donor is present in the solution. Generally, a cofactor is used as the electron donor in the KRED reduction reaction. The cofactor operates in combination with the KRED and/or GDH in the process. Suitable cofactors include, but are not limited to, $NADP^+$ (nicotinamide adenine dinucleotide phosphate), NADPH (the reduced form of $NADP^+$), $NAD^+$ (nicotinamide adenine dinucleotide) and NADH (the reduced form of $NAD^+$). Generally, the reduced form of the cofactor is added to the reaction mixture. Accordingly, the methods of the present disclosure are carried out wherein an electron donor is present selected from NADPH cofactor or NADH cofactor. In certain embodiments, the method can be carried out wherein the reaction conditions comprise an NADH or NADPH cofactor concentration of about 0.03-0.5 g/L, about 0.05-0.3 g/L, about 0.1-0.2 g/L, about 0.5 g/L, about 0.1 g/L, or about 0.2 g/L.

In some embodiments of the process, a cofactor recycling system is used to regenerate cofactor NADPH/NADH form $NADP^+/NAD^+$ produced in the reaction. A cofactor recycling system refers to a set of reactants that reduce the oxidized form of the cofactor (e.g., $NADP^+$ to NADPH) thereby allowing the KRED catalysis to continue. The cofactor recycling system may further comprise a secondary substrate and catalyst, for example, the substrate glucose, and the enzyme GDH, that catalyzes the reduction of the oxidized form of the cofactor by the reductant. Cofactor recycling systems to regenerate NADH or NADPH from $NAD^+$ or $NADP^+$, respectively, are known in the art and may be used in the methods described herein. Suitable exemplary cofactor recycling systems that may be employed include, but are not limited to, glucose and glucose dehydrogenase (GDH), formate and formate dehydrogenase (FDH), glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either $NADP^+$/NADPH or $NAD^+$/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

In some embodiments of the present disclosure, the cofactor recycling system can comprise glucose dehydrogenase (GDH), which is an $NAD^+$ or $NADP^+$-dependent enzyme that catalyzes the conversion of D-glucose (dextrose) and $NAD^+$ or $NADP^+$ to gluconic acid and NADH or NADPH, respectively. GDH enzymes suitable for use in the practice of the processes described herein include both naturally occurring GDHs, as well as non-naturally occurring GDHs. Naturally occurring glucose dehydrogenase encoding genes have been reported in the literature, e.g., the *Bacillus subtilis* 61297 GDH gene, *B. cereus* ATCC 14579 and *B. megaterium*. Non-naturally occurring GDHs generated using, for example, mutagenesis, directed evolution, and the like and are provided in PCT publication WO 2005/018579, and US publication Nos. 2005/0095619 and 2005/0153417.

In some embodiments, the co-factor recycling system can comprise a formate dehydrogenase (FDH), which is an $NAD^+$ or $NADP^+$-dependent enzyme that catalyzes the conversion of formate and $NAD^+$ or $NADP^+$ to carbon dioxide and NADH or NADPH, respectively. FDHs suitable for use as cofactor regenerating systems in the KRED catalyzed reaction described herein include naturally occurring and non-naturally occurring formate dehydrogenases. Suitable formate dehydrogenases are described in PCT publication WO 2005/018579. Formate may be provided in the form of a salt, typically an alkali or ammonium salt (for example, $HCO_2Na$, $KHCO_2NH_4$, and the like), in the form of formic acid, typically aqueous formic acid, or mixtures thereof. A base or buffer may be used to provide the desired pH.

In some embodiments, the co-factor regenerating system can comprise the same KRED enzyme that catalyzes the reduction of I-3 to I-4. In such an embodiment, the same KRED catalyzing the reduction of I-3 to I-4 also catalyzes the oxidation of a secondary alcohol (e.g., isopropanol to acetone oxidation) and thereby simultaneously reduces the $NAD^+$ or $NADP^+$ to NADH or NADPH. Accordingly, in some embodiments, the KRED catalyzed conversion of I-3 to I-4 can be carried out in the presence of a secondary alcohol (e.g., IPA) and without any coenzyme (e.g., GDH) present in the solution for the recycling of the NADPH or NADH cofactor. In such embodiments, the suitable reaction conditions can comprise an IPA concentration is about 55-75% (v/v), an NADPH or NADH cofactor loading of about 0.03-0.5 g/L, and wherein no cofactor recycling enzyme is present other than the KRED itself.

Suitable cofactor recycling systems for use in the KRED catalyzed conversion of compound I-3 to I-4 include the co-enzyme glucose dehydrogenase (GDH) coupled with the substrate glucose (L- or D-glucose). Suitable GDH cofactors include, but are not limited to, the GDH of polypeptide of SEQ ID NO. 3 and GDH of polypeptide of SEQ ID NO. 4, both of which are commercially available from Codexis Inc., Redwood City, Calif.

In one embodiment, compound I-5 is prepared by reacting compound I-4 with an acetonide protection agent:

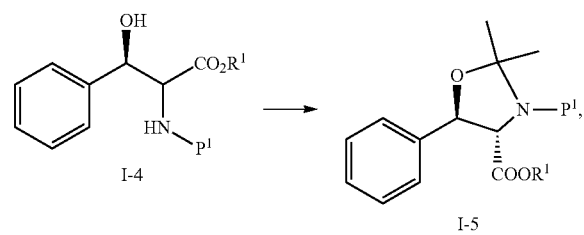

wherein $R^1$ is selected from the group consisting of $C_{1-6}$alkyl, benzyl and phenyl; and $P^1$ is selected from the group consisting of Ac, Bn, Boc, Bz, Cbz, DMPM, FMOC, Ns, Moz, and Ts. In one embodiment, $R^1$ is selected from the group consisting of methyl, ethyl, propyl, butyl and benzyl. In another embodiment, $P^1$ is Boc.

Suitable acetonide protection reagents include, but are not limited to, 2,2-dimethoxy propane, 2,2-diethoxylpropane, 2-methoxypropene and acetone. In one embodiment, the acetonide protection reagent is 2,2-dimethoxy propane.

The reaction from I-4 to I-5 can be carried out in the presence of a solvent. Suitable solvents include, but are not limited to, toluene, acetone, THF, IPAc, dichloromethane, EtOAc, MeCN, and mixtures thereof. In one embodiment, the solvent is a mixture of toluene and acetone.

The reaction from I-4 to I-5 can be carried out in the presence of an acid. Suitable acids include, but are not limited to, boron trihalides, organoboranes, HCl, $H_2SO_4$, TFA, $H_3PO_4$ and $TiCl_4$. In one embodiment, the acid is $BF_3$. In another embodiment, the $BF_3$ is in the form of boron trifluoride etherate ($BF_3 \cdot O(Et)_2$).

The reaction from I-4 to I-5 can be carried out at a temperature of 10° C. to 50° C., or more specifically, 20° C. to 40° C. It has been found that increasing the reaction temperature from 20° C. to 40° C. can increase the rate of reaction by 2-3 fold while not affecting the product profile.

In one embodiment, compound I-6 is prepared from compound I-5 with a reducing agent:

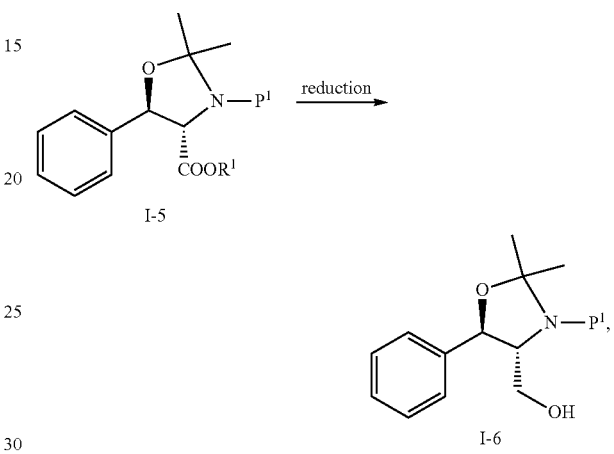

wherein $R^1$ is selected from the group consisting of $C_{1-6}$alkyl, benzyl and phenyl; and $P^1$ is selected from the group consisting of Ac, Bn, Boc, Bz, Cbz, DMPM, FMOC, Ns, Moz, and Ts. In one embodiment, $R^1$ is selected from the group consisting of methyl, ethyl, propyl, butyl and benzyl. In another embodiment, $P^1$ is Boc.

Suitable reducing agents include, but are not limited to, $LiAlH_4$, $LiBH_4$, $NaBH_4$—LiBr and DIBAL. In one embodiment, the reducing agent is $LiAlH_4$. In another embodiment, the reducing agent is $LiBH_4$. In yet another embodiment, the reducing agent $LiBH_4$ can be generated in situ, for example by the use of a combination of $NaBH_4$ and LiBr.

The amount of the reducing agent is typically 0.8 to 1.6 equiv., or more specifically, 1.0 to 1.4 equiv.

In one embodiment, the reduction from I-5 to I-6 is carried out at a temperature of 0° C. to 60° C., or more specifically, 0° C. to 35° C., or even more specifically, 20° C. to 30° C. In one embodiment, the temperature is 20° C. to 30° C.

In one embodiment, the oxidation of compound I-6 to compound I-7 is carried out in the presence of a catalyst with an oxidizing agent:

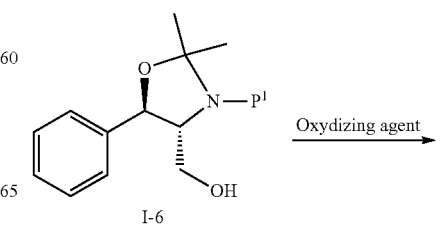

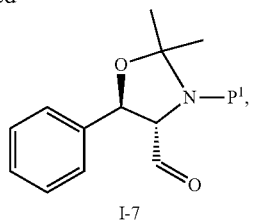

I-7 wherein P¹ is selected from the group consisting of Ac, Bn, Boc, Bz, Cbz, DMPM, FMOC, Ns, Moz, and Ts. In one embodiment, P¹ is Boc.

Suitable oxidizing agents include, but are not limited to, NaOCl, NaClO$_2$, hydrogen peroxide, Swern oxidation and variants such as pyridine sulfur trioxide, PCC, and DCC. In one embodiment, the oxidizing agent is NaOCl.

The amount of the oxidizing agent is typically 1.1 equiv. to 1.3 equiv., or more specifically, 1.2 equiv. to 1.25 equiv. In one embodiment, the amount of the oxidizing agent is 1.25 equiv.

Suitable catalysts for the above oxidation reaction include, but are not limited to, TEMPO and TEMPO analogues. In one embodiment, the catalyst is TEMPO.

One advantage of the presently described process is that compound I-7 from the oxidation step can be used directly in the next Horner Wadsworth Emmons (hereinafter, "HWE") step to obtain compound I-8. This one pot process eliminates the need for solvent switch and can increase the yield and reduce cost.

In one embodiment, the oxidation step from I-6 to I-7 can be carried out in the presence of a solvent. Suitable solvents include, but are not limited to, THF, MTBE, CH$_2$Cl$_2$, MeCN, toluene and mixtures thereof. In one embodiment, the solvent is a mixture of toluene and MeCN. In another embodiment, the solvent is a mixture of CH$_2$Cl$_2$ and MeCN.

In one embodiment, the HWE reaction between I-7 and A-4 is carried out in the presence of a solvent:

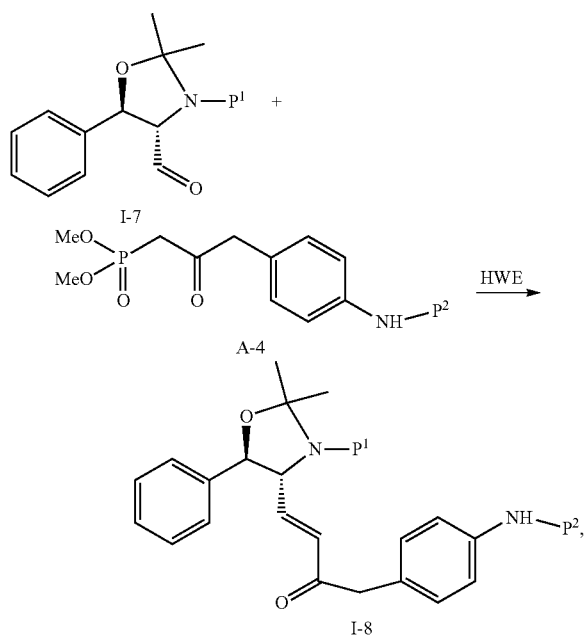

wherein P¹ and P² are each independently selected from the group consisting of Ac, Bn, Boc, Bz, Cbz, DMPM, FMOC, Ns, Moz, and Ts. In one embodiment, both P¹ and P² are Boc.

Suitable solvents include, but are not limited to, THF, MTBE, CH$_2$Cl$_2$, MeCN, toluene and a mixture comprising two of the foregoing solvents. In one embodiment, the solvent is the mixture of toluene and MeCN.

The HWE reaction is typically carried out at a temperature of −10 to 50° C., or more specifically, 0 to 40° C. In one embodiment, the temperature is 0 to 25° C. In another embodiment, the temperature is 40° C.

The HWE reaction is typically carried out in the presence of a base or a salt. In one embodiment, the base is a tertiary amine. In another embodiment, the base is N,N-diisopropylethylamine (DIPEA).

In one embodiment, the salt is lithium halide, or more specifically, LiCl or LiBr.

In the HWE reaction, an impurity compound I-21 (aldol dimmer by-product) may be formed in addition to compound I-8:

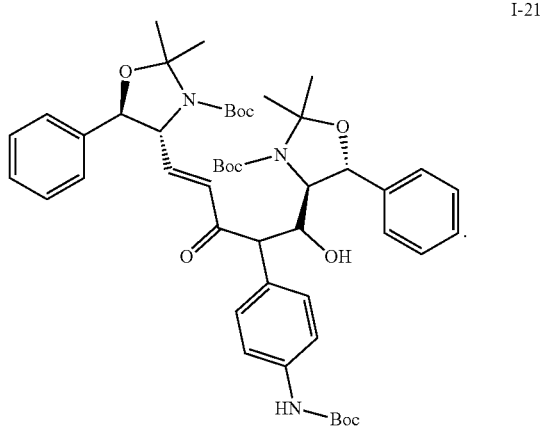 [SMILES: CC(C)(C)OC(=O)Nc1ccc(C(C(=O)/C=C/[C@@H]2[C@@H](c3ccccc3)OC(C)(C)N2C(=O)OC(C)(C)C)C(O)[C@@H]2[C@@H](c3ccccc3)OC(C)(C)N2C(=O)OC(C)(C)C)cc1]

It has been found that by adjusting pH to between 6.5 and 7.0 after the reaction, higher purity compound I-8 can be obtained with improved yield. Additionally, addition of more reactant compound A-4 has been shown to drive the impurity I-21 to product I-8. In one embodiment, addition of an extra 0.2 equiv. of A-4 can reduce the level of I-21 to from 8 LCAP to 2 LCAP.

Increasing the reaction temperature can speed up the conversion to the desired product compound I-8 and reduce the level of the byproduct compound I-21.

By changing the reaction from a batch process to an addition controlled process, the yield of compound I-8 can be improved and the level of byproduct compound I-21 can be reduced. For example, by adding reactant compound I-7 to a solution containing reactant compound A-4, the level of I-21 can be decreased and the yield of compound I-8 improved.

In one embodiment, a solution containing 1.2 equiv of A-4, 3 equiv. of DIPEA and 3 equiv. of LiCl in 5 volumes of MeCN was prepared and warmed to 40° C. A toluene stream of compound I-7 was then added to this mixture over 3 h, after an additional 30 min aging conversion to product was complete. The level of impurity I-21 was about ~1 LCAP. Sampling the reaction at 1 h intervals showed there was no build-up of compound I-7 in the reaction mixture. After work up the product was isolated with a 90% isolated yield.

It has also been found that using slightly smaller amount of reactant A-4 does not negatively affect the yield of compound I-8. In one embodiment, 1.0 instead of 1.2 equiv. of compound A-4 was used and high yield was still obtained.

Compound A-4 used in the HWE reaction can be prepared from compound A-1:

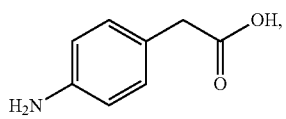

using similar synthetic steps and conditions as described in A General Procedure for the Preparation of β-Ketophosphonates, Maloney et. al., J. Org. Chem., 74, page 7574-7576 (2009).

In one embodiment, the reduction of compound I-8 to produce compound I-9 is carried out in the presence of a catalyst:

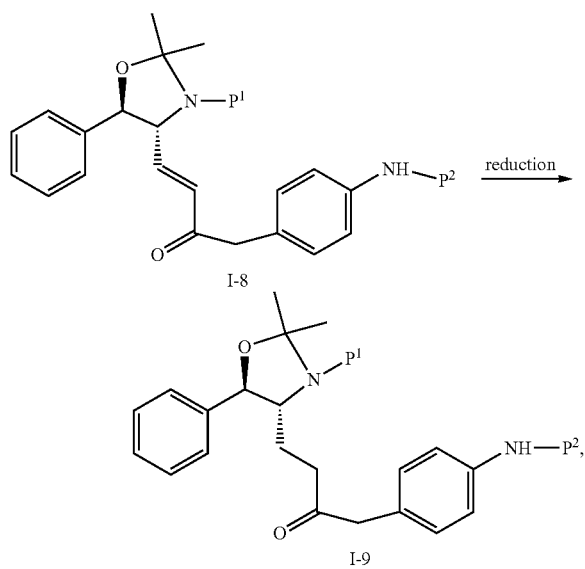

wherein $P^1$ and $P^2$ are each independently selected from the group consisting of Ac, Bn, Boc, Bz, Cbz, DMPM, FMOC, Ns, Moz, and Ts. In one embodiment, both $P^1$ and $P^2$ are Boc.

Suitable catalysts include, but are not limited to, Pd, Raney Ni, Pt, $PdCl_2$, and $Pd(OH)_2$. In one embodiment, the catalyst is 5% Pd/C.

In another embodiment, the reduction from I-8 to I-9 is carried out in the presence of a solvent. Suitable solvents include, but are not limited to, THF, MTBE, $CH_2Cl_2$, MeCN, toluene, methanol, ethanol, 2-propanol and mixtures thereof. In one embodiment, the solvent is THF.

In another embodiment, the reduction reaction is carried out using hydrogen gas at a pressure of 2 to 300 psig, preferably about 40 psig, in the presence of a catalyst.

In one embodiment, compound I-9 reacts with an acid to produce compound I-10 through a cyclization reaction:

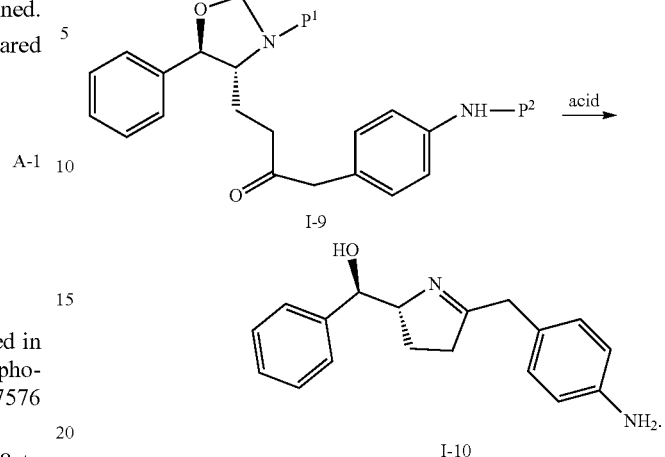

Suitable acids include, but are not limited to, HCl, HBr, TFA, $MeSO_3H$, TfOH, $H_2SO_4$, para-toluenesulfonic acid, and other sulfone acids such as $RSO_3H$ wherein R is $C_{1-6}$alkyl, aryl or substituted aryl. In one embodiment, the acid is HCl.

In one embodiment, HCl is used as acid and an HCl salt of compound I-10 is obtained. In one embodiment, the HCl salt is in the form of bis-HCl salt. In another embodiment, the bis-HCl salt is in the form of a mono-hydrate. In another embodiment, the mono-hydrate of the bis-HCl salt of compound I-10 is a crystalline material.

The conversion from I-9 to I-10 can be carried out at a temperature of 0 to 40° C., or more specifically, 15 to 25° C., or even more specifically, 20 to 25° C. In one embodiment, the temperature is 20 to 25° C.

In one embodiment, compound I-10 is reduced to compound I-11 in the presence of a catalyst:

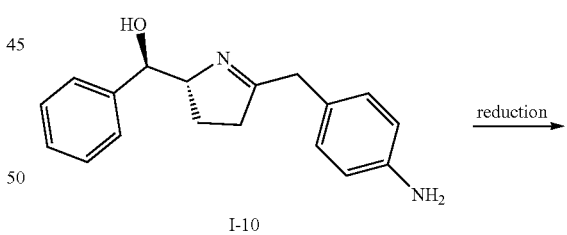

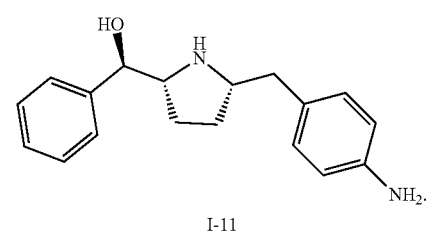

The reaction conditions for the conversion from I-10 to I-11 can be controlled so a cis-selective hydrogenation process is obtained. In one embodiment, the cis-selective hydrogenation is carried out in the presence of a catalyst. Suitable catalysts include, but are not limited to Pt on alumina, Pd on alumina, Pd/C, Pd(OH)$_2$—C, Raney Ni, Rh/C, Rh/Al, Pt/C, Ru/C and PtO$_2$. In one embodiment, the catalyst is Pt on alumina.

In another embodiment, the cis-selective hydrogenation from I-10 to I-11 is carried out in the presence of HMDS, which can protect the hydroxy group in situ and therefore improve the diastereo selectivity. Other suitable protecting reagents include, but are not limited to, TMSCl, TESCl, and TBDMSCl.

In one embodiment, compound I-11 is obtained in the form of a crystalline anhydrous free base. In another embodiment, compound I-11 is obtained in the form of a crystalline free base hemihydrate.

As used herein, the term "alkyl" means both branched- and straight-chain saturated aliphatic hydrocarbon groups having the specified number of carbon atoms. For example, $C_{1-6}$alkyl includes, but is not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu), isopentyl, sec-pentyl, tert-pentyl and isohexyl.

As used herein, the term "aryl" refers to an aromatic carbocycle. For example, aryl includes, but is not limited to, phenyl and naphthale.

Throughout the application, the following terms have the indicated meanings unless noted otherwise:

| Term | Meaning |
| --- | --- |
| Ac | Acyl (CH$_3$C(O)—) |
| Aq | Aqueous |
| Bn | Benzyl |
| BOC (Boc) | t-Butyloxycarbonyl |
| Boc$_2$O | Di-tert-butyl dicarbonate |
| Bz | Benzoyl |
| ° C. | Degree celsius |
| Calc, or calc'd | Calculated |
| Cbz | Carbobenzyloxy |
| CDI | 1,1'Carbonyldiimidazole |
| DCC | N,N'-Dicyclohexycarbodiimide |
| DCM | Dichloromethane |
| DKR | Dynamic kinetic resolution |
| DMAc | N,N-dimethylacetamide |
| DMAP | 4-Dimethylaminopyridine |
| DMF | N,N-dimethylformamide |
| DMPM | 3,4-Dimethoxybenzyl |
| DMSO | Dimethyl sulfoxide |
| EDC | 1-Ethyl-3-(3-dimethylaminopropyl) carbodiimide |
| Eq. or equiv. | Equivalent(s) |
| ES-MS and ESI-MS | Electron spray ion-mass spectroscopy |
| Et | Ethyl |
| EtOAc | Ethyl acetate |
| FMOC | 9-Fluorenylmethyloxycarbonyl |
| g | Gram(s) |
| h or hr | Hour(s) |
| HATU | O-(7-Azabenzotriazol-1-yl)-N,N,N',N'-tetramethyluronium hexafluorophosphate |
| HBTU | O-(Benzotriazol-1-yl)-N,N,N',N'-tetramethyluronium hexafluorophosphate) |
| HCl | Hydrogen chloride |
| HMDS | Hexamethyldisilazane |
| HPLC | High performance liquid chromatography |
| HOAc | Acetic acid |
| HOBT | 1-Hydroxy-1H-benzotriazole |
| HOPO | 2-Hydroxypyridine-N-oxide |
| IPA | Isopropyl alcohol |
| kg | Kilogram(s) |
| LC/MS or LC-MASS | Liquid chromatography mass spectrum |
| L | Liter(s) |
| LAH or LiAlH$_4$ | Lithium aluminium hydride |
| LCAP | Liquid Chromatography Area Percent |
| LiBH$_4$ | Lithium borohydride |
| M | Molar(s) |
| Me | Methyl |
| MeCN | Acetonitrile |
| MeOH | Methanol |
| min | Minute(s) |
| mg | Milligram(s) |
| mL | Milliliter(s) |
| mmol | Millimole(s) |
| Moz or MeOZ | p-Methoxybenzyl carbonyl |
| MTBE | Methyl tert-butyl ether |
| NADP | Nicotinamide adenine dinucleotide phosphate sodium salt |
| nM | Nanomolar |
| Ns | 4-Nitrobenzene sulfonyl |
| PCC | Pyridinium chlorochromate |
| 5% Pd/C | Palladium, 5 weight percent on activated carbon |
| Ph | Phenyl |
| r.t. or rt or RT | RT |
| Sat. | Saturated |
| TBDMSCl | Tert-Butyldimethylsilyl chloride |
| TEA or Et$_3$N | Triethylamine |
| TEMPO | 1-Oxyl-2,2,6,6-tetramethylpiperidine |
| TESCl | Triethylchlorosilane |
| TFA | Trifluoroacetic acid |
| THF | Tetrahydrofuran |
| TMSCl | Trimethylchlorosilane |
| Ts | p-Toluene sulfonyl |

Reaction Schemes below illustrate the synthetic steps, reagents and conditions employed in the synthesis of the compounds described herein. The synthesis of compound I-11 which is the subject of this invention may be accomplished by one or more of similar routes.

Example 1
Preparation of Compound i-11 from Starting Compound i-1
Scheme 1
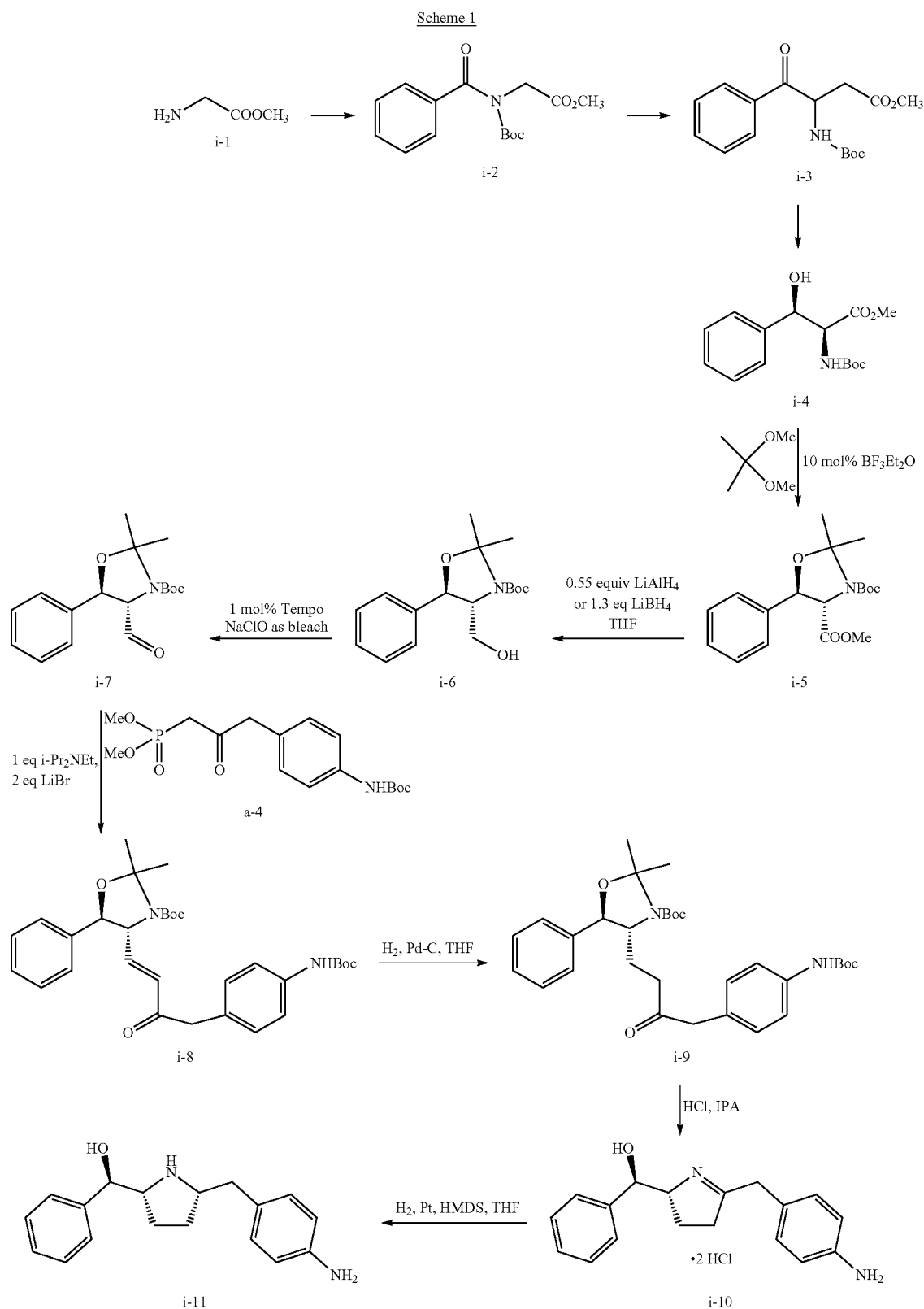

In Scheme 1, one-pot through process produced keto amide i-3 from starting material i-1. An enzymatic DKR reduction produced i-4 from i-3. After protection, ester i-5 was reduced to alcohol i-6 with LAH or LiBH$_4$.

Once compound i-6 was obtained, it was converted to i-7 by TEMPO oxidation. For the TEMPO oxidation and subsequent HWE coupling step, a one-pot through process was used such that the crude stream of the aldehyde i-7 after phase cut was used directly for the HWE reaction to avoid solvent switch. Unsaturated ketone i-8 was isolated over 5 steps. Finally, compound i-8 was converted to compound i-11 through i-9 and i-10. Detailed experimental conditions are described below.

Step 1. Preparation of Compound i-3 from Compound i-1

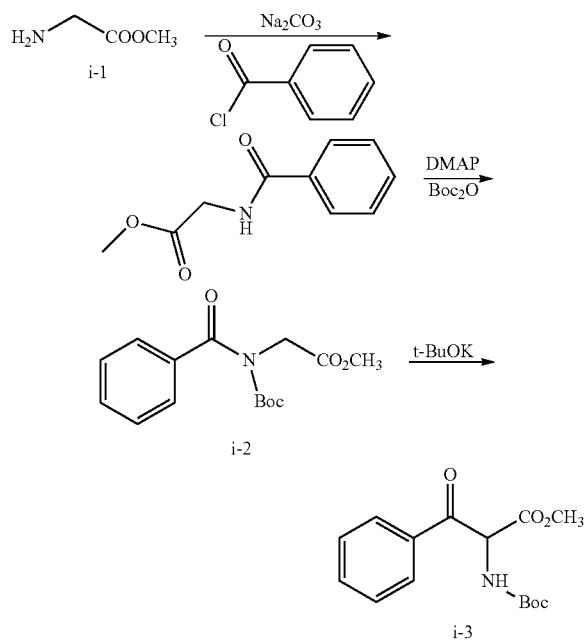

To a mixture of Na$_2$CO$_3$ (110 g, 1.034 mol) in water (606 mL) and EtOAc (606 mL) at 0-5° C. was added glycine methyl ester (i-1, 119 g, 948 mmol) in portions over 30 min. The resulting slurry was aged for additional 15-30 min, PhCOCl (100 ml, 0.862 mol) was then 10 added dropwise over 1.5 h at 0-5° C. After aging additional 1 h at 0-5° C., the reaction mixture was warmed to 25° C. to form a homonogenous biphasic solution. The separated organic phase was azetropically concentrated and solvent switched to MeCN. A final volume of about 600 mL was obtained.

DMAP (43.1 mmol, 5.26 g) was added and then a solution of Boc$_2$O (0.948 mol, 207 g) in MeCN (200 mL) was added at RT dropwsie over 2-3 h. The reaction solution was aged at RT for ~6 h. The batch was vacuum degassed with N$_2$ three times to remove CO$_2$ generated in the amidation step. THF (540 mL, KF<500) was added to the reaction solution. A solution of t-BuOK (1.12 mol, 128 g, 97%) in THF (670 ml) was then added at 0-10° C. dropwise over 1-2 h. The reaction solution was aged at 0-5° C. for 1 h.

The reaction was then quenched with 15 wt % citric acid in water (0.431 mol, 91 g citric acid in 515 mL H$_2$O) at <10° C. The organic phase was washed with 480 mL of half saturated NaCl in water and solvent switched to IPA to a final volume of ~1.25 L with ~10% water in IPA at <45° C.

The batch was warmed to 40-50° C. Water (1250 mL) was added dropwise at 40-50° C. over 2 h resulting in a slurry.

The slurry was cooled to ambient temperature (20° C.) and aged for 1-2 h before filtration. The wet cake of i-3 was displacement washed with 30% IPA in water (640 mL×2). Suction dry at RT or vacuum oven dry at <50° C. with dry N$_2$ sweep gave 227 g of white crystalline solid i-3 with 90% yield as determined by HPLC described below.

| HPLC Method |
| --- |
| Column: Asentis Express C18, 4.6 × 150 mm, 2.7 μm particle size; Column Temp: 30° C.; Flow Rate: 1.5 mL/min; UV Detection: 210 nm; Mobile Phase: A: 0.1% H$_3$PO$_4$ B: acetonitrile |

| Mobile Phase Program: | | | | | |
| --- | --- | --- | --- | --- | --- |
| Time, min | 0 | 1 | 5 | 7 | 9 |
| A % | 95 | 95 | 60 | 10 | 10 |
| B % | 5 | 5 | 40 | 90 | 90 |

Step 2. Preparation of Compound i-4 from Compound i-3 Through DKR Reduction

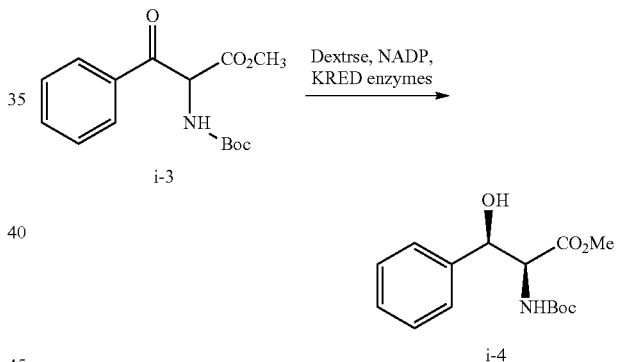

To a solution of K$_2$THPO$_4$ (14.1 g) in 80 mL water at RT was added dextrose (9.8 g) followed by NADP (360 mg), KRED enzyme of SEQ ID NO. 2 (290 mg) and a cofactor recycling system of SEQ ID NO. 4 (115 mg). The resulting homogenous solution was pH adjusted to a minimum of 7.5 with 2M NaOH prior to use.

A solution of i-3 (12.0 g) in DMSO (36 ml) at 30° C. was added dropwise to the above aqueous enzyme solution at 30° C. over 4 h under vigorous agitation. 2M NaOH (~21 mL) was added dropwise to maintain the reaction mixture at pH of 7.3 to 7.7. Once 90% (~19 mL) of 2M NaOH solution was added, the reaction temperature was raised to 35° C. until >95% conversion was achieved.

IPA (91 mL) and MTBE (49 mL) were added at RT. The organic layer was separated. The aqueous phase was extracted with IPA/MTBE (140 ml, IPA:MTBE=20:80). The combined organic phase was washed with brine (50 mL, 10% w/v brine) and the crude product containing compound i-4 was directly used for the next step.

Using the following HPLC method, the retention times of i-3 and i-4 were about 8.8 and 7.8 min, respectively.

| HPLC Method |
| --- |
| Column: Ace 3 Column C18, 3 × 150 mm, 3 μm particle size<br>Column Temp: 30° C.; Flow Rate: 0.75 mL/min;<br>UV Detection: 215 nm; Mobile Phase: A: Formate Buffer, pH 4 (1.26 g HCO₂Na and 0.79 mL HCO₂H in 1 L H₂O)<br>B: Acetonitrile |

| Mobile Phase Program: | Time (min) | % B |
| --- | --- | --- |
| | 0 | 5 |
| | 10 | 95 |

| Chiral SFC Method |
| --- |
| Column: Chiralpak IC, 250 × 4.6 mm, 5 μm particle size<br>Column Temp: 35° C.; Flow Rate: 2 mL/min;<br>UV Detection: 210 nm; |

| Mobile Phase Program: | | | | |
| --- | --- | --- | --- | --- |
| Time, min | 0 | 2 | 13 | 15 |
| A % | 95 | 95 | 60 | 60 |
| MeOH % | 5 | 5 | 40 | 40 |

Step 3. Preparation of Compound i-5 from Compound i-4 through Acetonide Protection

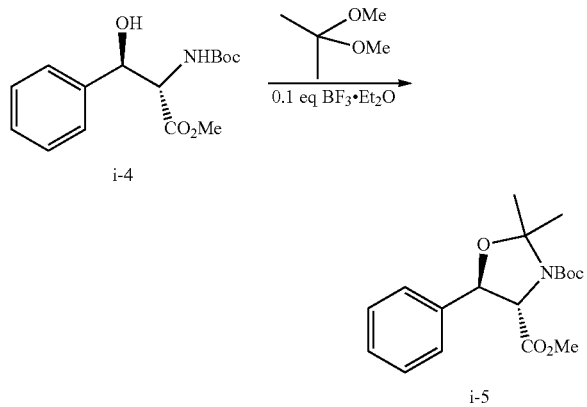

To a toluene solution of the i-4 ester (10.6 g, in ~25 to 30 mL toluene, crude solution from previous DKR step) were added 50 mL of acetone and 20 ml of 2,2-dimethoxy propane. A solution of BF₃ etherate (0.43 mL) in toluene (2 mL) was then added via a syringe pump at RT over 2 h. The reaction solution was aged at RT for 15 h. The conversion was found to be >97% by HPLC. The retention times of i-4 and i-5 were about 4.5 min and 6.5 min, respectively.

Et₃N (0.5 mL) was added dropwise. After aging for additional 15 min at ambient temperature, the solution was solvent switched to toluene (~30 mL) while most of the acetone was removed in vacuum. MTBE (60 mL) was added and the organic phase was washed with 5% NaHCO₃/brine (40 mL). Organic phase was azetropically dried and solvent switched to toluene to a final volume of ~35-40 mL.

| HPLC Method |
| --- |
| Column: Asentis Express C18, 4.6 × 150 mm,<br>2.7 μm particle size<br>Column Temp: 40° C.; Flow Rate: 1.5 mL/min;<br>UV Detection: 210 nm;<br>Mobile Phase: A: 0.1% H₃PO₄ B: acetonitrile |

| Mobile Phase Program: | | | | |
| --- | --- | --- | --- | --- |
| Time, min | 0 | 5 | 7 | 10 |
| A % | 95 | 15 | 5 | 5 |
| B % | 5 | 85 | 95 | 95 |

Step 4. Preparation of Compound i-6 Through Reduction of Compound i-5

Compound i-6 can be prepared from the reduction of compound i-5 under two alternative conditions.

Option 1: LAH Reduction:

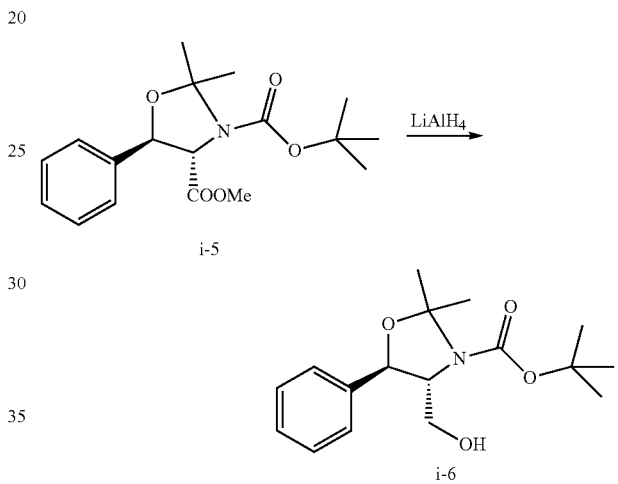

To a crude i-5 ester solution in toluene (8.28 g assay, from previous protection step, in ~2.5-3 vol of toluene) was added 40 mL of THF. Then, the solution was cooled to 0° C. LiAlH₄ (2M solution in THF, 6.9 mL) was added dropwise over 1 h while the internal temperature was kept at 0-5° C. The reaction solution was aged for additional 0.5-1 h. Conversion was >99% by HPLC. At 0-5° C., 0.52 mL of H₂O in 2.0 mL of THF followed by 0.52 mL of 15% NaOH then followed by 1.56 mL of H₂O were added slowly. The slurry mixture was warmed up to RT and filtrated through Solka Floc. The wet cake was washed with THF (25 mL) and toluene (16 mL).

Assay yield of 91% was obtained using the following HPLC method. The retention times of i-5 and i-6 were about 6.5 min and 5.7 min, respectively.

| HPLC Method |
| --- |
| Column: Asentis Express C18, 4.6 × 150 mm,<br>2.7 μm particle size; Column Temp: 40° C.;<br>Flow Rate: 1.5 mL/min; UV Detection: 210 nm;<br>Mobile Phase: A: 0.1% H₃PO₄ B: Acetonitrile |

| Mobile Phase Program: | | | | |
| --- | --- | --- | --- | --- |
| Time, min | 0 | 5 | 7 | 10 |
| A % | 95 | 15 | 5 | 5 |
| B % | 5 | 85 | 95 | 95 |

Option 2: LiBH₄ Reduction

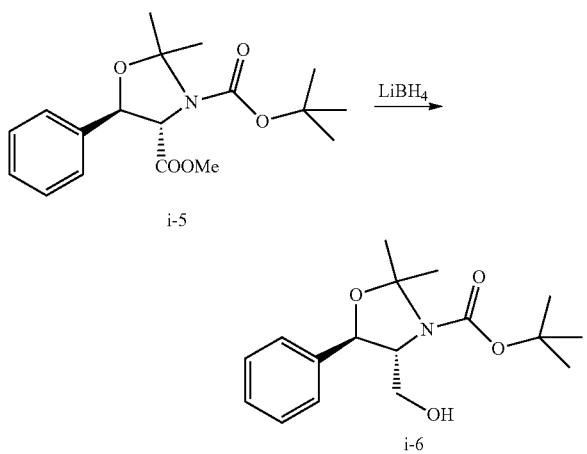

A crude solution of i-5 ester in toluene (11.1 g assay, from previous protection step, in ~2.5-3 vol of toluene) was added to a mixture of LiBH₄ (0.937 g) in THF (60 mL) over 15-30 min. Then, the reaction solution was aged for 15 h at 35° C. The conversion was >97% by HPLC.

The reaction solution was cooled down to RT and inversely quenched to a solution of 10% NH₄Cl (40 mL) while the internal temperature was maintained below 5° C. with external cooling. The quenched solution was aged at ambient temperature for 2-3 h or until the evolution of H₂ gas ceased. MTBE (100 mL) was added. Aqueous layer was discarded and organic layer was solvent switched to toluene to a final volume of ~40 mL, which was directly used in the subsequent oxidation step. Assay yield was 92% and aqueous loss was 1.2%.

Step 5. Preparation of Compound i-7 by TEMPO Oxidation of Compound i-6

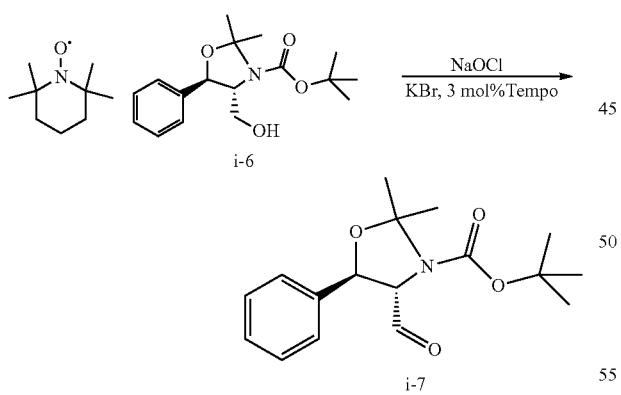

To a solution of i-6 alcohol in toluene (20 g assay, ~60 mL) was added acetonitrile (120 mL) at RT. KBr (1.16 g), NaHCO₃ (1.8 g) and water (40 mL) were then charged resulting in a biphasic mixture. The biphasic mixture was cooled to 5° C. and TEMPO (305 mg) was added. Then, NaClO solution (Clorox; 6 wt %; 101 g) was added dropwise at 0-5° C. over 2 h. After addition, the reaction was stirred at 5° C. for ~30 min. Conversion of >96% was obtained.

The reaction was quenched by dropwise addition of 10% sodium sulfite (50 mL) at 5° C. The organic layer was separated and directly used for the subsequent HWE coupling step without further purification. The assay yield was 17.5 g (88%) by ¹H NMR using DMAc as internal standard.

Retention times of i-6 and i-7 using the following HPLC method were about 3.3 min and 3.9 min, respectively.

| HPLC Method |
|---|
| Column: Zorbax, Eclipse Plus C18, 4.6 × 50 mm, 1.8 μm particle size; Column Temperature: 22° C.; Flow Rate: 1.5 mL/min; UV Detection: 210 nm; Mobile Phase: A: 95/5/0.1, H₂O/Methanol/H₃PO₄ B: 95/5, MeCN/methanol |

| Mobile Phase Program: | | | |
|---|---|---|---|
| Time, min | 0 | 5 | 6 |
| A % | 60 | 10 | 10 |
| B % | 40 | 90 | 90 |

Step 6. Preparation of i-8 by Horner Wadsworth Emmons (HWE) Coupling Reaction

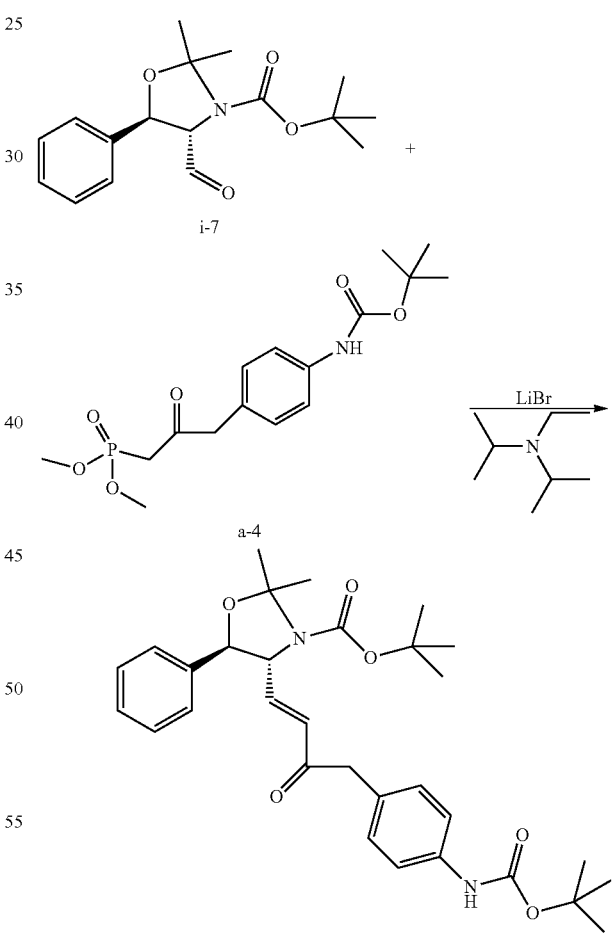

To a solution of i-7 aldehyde in wet toluene/acetonitrile (162 g solution; 17.5 g assay; 10.81 wt %) obtained above at −10° C. were added acetonitrile (140 mL), phosphonate a-4 (24.6 g) and LiBr (14.9 g) while the internal temperature was maintained below 0° C.

The reaction was warmed up to 0° C., and Hunig's base (22.2 g) was charged at 0-5° C. dropwise over 2 h. The resulting reaction mixture was stirred at 0-5° C. for 2-4 h and allowed to warm to RT, followed by aging at RT for 12 h. HPLC showed conversion (product/(product+aldehyde)) of >99%.

The slurry was cooled to 5° C., and a 10% aqueous solution of citric acid (~75 g) was added dropwise to adjust the pH to 6.5-7.0 while maintaining the batch temperature at 0-5° C. The aqueous phase was separated at 0-5° C. and discarded.

The organic layer was washed with saturated NaHCO₃ (57 mL) and with H₂O (57 mL) successively. The organic phase was solvent switched to IPA to a final volume of ~192 mL. The product was gradually crystallized during the distillation.

Water (16.4 mL, 0.6 vol.) was added, and the resulting slurry was heated to 49° C. to give a homogeneous solution. The resulting solution was cooled to 40° C. and seeded (0.27 g). The resulting mixture was aged at 40° C. for 2 h to establish a seed bed, and H₂O (93 mL) was charged dropwise at 40° C. over 3 h, followed by aging at 40° C. for 1 h. The slurry was allowed to cool to 5-10° C. over 2 h, followed by aging at 5-10° C. for 2 h.

The wet cake was washed with 50% H₂O/IPA (a 164 mL cold displacement wash followed by a 110 mL slurry wash). Suction dried under nitrogen gave the product as an off-white solid (24.9 g, 100 wt %, >99 LCAP, 80% isolated yield from aldehyde).

Using the following HPLC method, the retention times of i-7, a-4 and i-8 were about 3.0 min, 1.2 min and 3.8 min, respectively.

| HPLC Method |
| --- |
| Column: Zorbax, Eclipse Plus C18, 4.6 × 50 mm, 1.8 μm particle size Column Temp: 40° C.; Flow Rate: 1.5 mL/min; UV Detection: 210 nm; Mobile Phase: A: 0.1% H₃PO₄ B: MeCN |

| Mobile Phase Program: | | | |
| --- | --- | --- | --- |
| Time, min | 0 | 3 | 7 |
| A % | 60 | 10 | 10 |
| B % | 40 | 90 | 90 |

Step 7. Preparation of Compound i-9 from Compound i-8

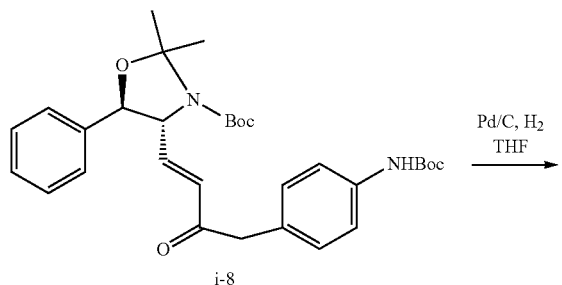

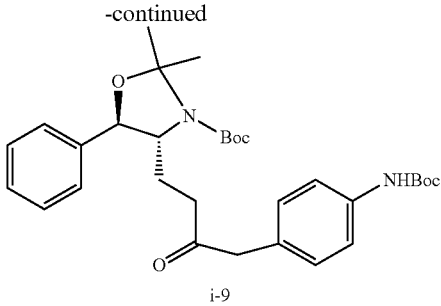

THF (84 g) followed by enone i-8 (19.07 g) and 10% Palladium on carbon (0.95 g) were charged to a hydrogenation vessel. The batch was hydrogenated for 90 min at 25° C. until uptake of hydrogen had ceased. The catalyst was removed through filtration of a bed of solka floc. The filtered residues were washed with THF (84 g). The combined organic phase was solvent switched to IPA to a final volume of 142 mL, which was directly used in the next step. Assay yield of 93% was obtained (17.8 g of i-9).

Using the following HPLC method, the retention times of i-8 and i-9 were about 11.2 min and 11.4 min, respectively.

| HPLC method |
| --- |
| Column: HiChrom ACE C18 (250 × 4.6 mm), 3 μm particle size; Column Temperature: 30° C.; Flow rate: 1.0 mL/min; Detection: 210 nm, 254 nm; Mobile phase: A: 1 mL of phosphoric acid (85%) dissolved in 1 L of H₂O B: MeCN |

| Mobile Phase Program: | | | | | |
| --- | --- | --- | --- | --- | --- |
| Time, min | 0 | 5 | 8 | 15 | 16 | 20 |
| A% | 95 | 65 | 5 | 5 | 95 | 95 |
| B% | 5 | 35 | 95 | 95 | 5 | 5 |

Step 8. Preparation of Compound i-10 from Compound i-9

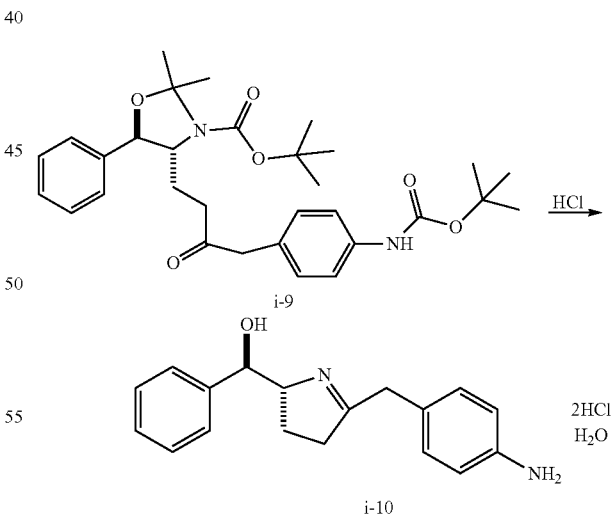

To a solution of the N-Boc-Ketone aniline i-9 (26.1 assay kg) in IPA (~125 g/L) was added 4N HCl in IPA (220.8 L) at RT. The reaction mixture was stirred vigorously at 20-25° C. for 24 h. The batch was distilled under reduced pressure, at constant volume by charging IPA up to one batch volume, to remove HCl. The batch was then concentrated to a final volume of ~215 L.

The resulting slurry was heated to 45° C., and IPAc (~430 L) was slowly added to the batch over 2-3 h. The slurry was then cooled to ~20° C. over 1-2 h and aged overnight. The batch was filtered, and the cake was washed with a 1:2 mixture of IPA:IPAc (52 L) followed by IPAc (52 L). The wet cake was dried at 45° C. under nitrogen atmosphere to give the cyclic imine bis-HCl monohydrate salt i-10 (16.1 kg). The isolated yield of 94% was obtained.

Using the same HPLC method as in Step 7 (i-8 to i-9), the retention times of i-9 and i-10 (bis-HCl salt) were about 11.3 min and 8.3 min, respectively.

Step 9. Preparation of Compound i-11 from Compound i-1°

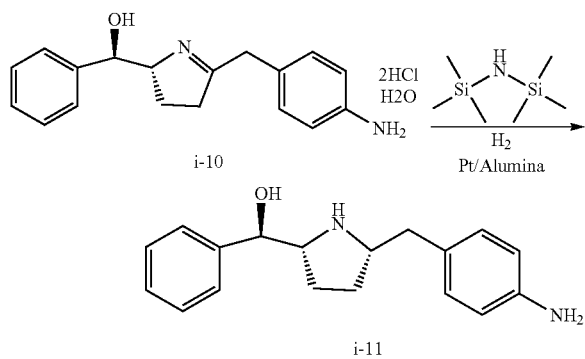

To a mixture of imine dihydrochloride monohydrate i-10 (12.0 g, 98.5 wt %) in THF (86 mL) under $N_2$ was added hexamethyldisilazane (10.95 g) while maintaining the batch temperature below 25° C. The resulting slurry was stirred vigorously at ambient temperature for 2 h.

A 300 mL autoclave was charged with a suspension of 5% platinum on alumina (0.605 g) in THF (32 mL), followed by the substrate slurry prepared above. The resulting mixture was stirred at RT under hydrogen (40 psig) until the hydrogen uptake ceased. The completion of the hydrogenation was confirmed by HPLC, and the vessel was inerted with nitrogen.

The reaction mixture was discharged, and the vessel rinsed with 96 mL of THF. The batch was filtered through a pad of Solka Floc, and the pad was rinsed with the THF vessel rinse (~96 mL). The combined filtrate was stirred with 0.5 M hydrochloric acid (129 mL) at ambient temperature for 1 h. The aqueous layer was separated. IPAc (39 mL) followed by 5 N sodium hydroxide (~15 mL) was added to adjust the pH to 10.0 with vigorous stirring.

The organic layer (~120 mL) was separated and treated with AquaGuard Powder (Meadwestvaco) (2.4 g) at RT for 2 h. The solution was filtered through a pad of Solka Floc, and the pad was rinsed with 2-propanol (18 mL). The combined filtrate was concentrated to 70 mL. The solution was distilled at the constant volume by feeding a total of 140 mL of 2-propanol, maintaining the batch temperature at 33-35° C. The resulting solution was concentrated to ~34 mL and heated to 50° C., followed by addition of $H_2O$ (6.3 mL). The resulting solution was cooled to 41-43° C. and seeded with pyrrolidine aniline hemihydrate (42 mg). The resulting mixture was aged at 41-43° C. for 1 h to establish a seed bed.

Water (60.9 mL) was charged at 41-43° C. over 6 h, and the resulting mixture was allowed to cool to 10° C. over 3 h, followed by aging at 10° C. for 2 h. The solids were collected by filtration and washed with 25% 2-propanol/$H_2O$ (50 mL). The wet cake was suction-dried at ambient temperature under nitrogen to afford 7.68 g of pyrrolidine aniline i-11 as hemihydrate.

$^1$H NMR ($d_6$-DMSO) δ 7.27 (m, 4H), 7.17 (m, 1H), 6.81 (d, J=8.1, 2H), 6.45 (d, J=8.1 Hz, 2H), 5.07 (s, br, 1H), 4.75 (s, 2H), 4.18 (d, J=7.0 Hz, 1H), 3.05 (m, 2H), 2.47 (dd, J=13.0, 6.7 Hz, 1H), 2.40 (dd, J=13.0, 6.6 Hz, 1H), 1.53 (m, 1H), 1.34 (m, 1 HO, 1.22 (m, 2H).

$^{13}$C NMR ($d_6$-DMSO) δ 146.5, 144.3, 129.2, 127.8, 127.4, 126.8, 126.7, 114.0, 76.8, 64.4, 60.1, 42.1, 30.2, 27.2.

Using the following HPLC method, the retention times of i-10 (bis-HCl salt) and i-11 were about 8.3 min and 8.5 min, respectively.

| HPLC Method |
|---|
| Column: Waters Xbridge C18, 150 × 4.6 mm, 3.5 µm; Column Temperature: 25° C.; Flow rate: 1 mL/min; Detection: 210 nm, 254 nm; Mobile phase: A: Acetonitrile B: 0.1% aqueous $NH_4OH$ adjusted to pH 9.5 with H |

| Mobile Phase Program: | | | | | |
|---|---|---|---|---|---|
| Time, min | 0 | 4 | 8 | 10 | 17 |
| A % | 99 | 65 | 65 | 30 | 30 |
| B % | 1 | 35 | 35 | 70 | 70 |

Example 2

Preparation of Compound i-8 from Compound i-1—Alternative Conditions

Step 1. Preparation of Compound i-3 from Compound i-1

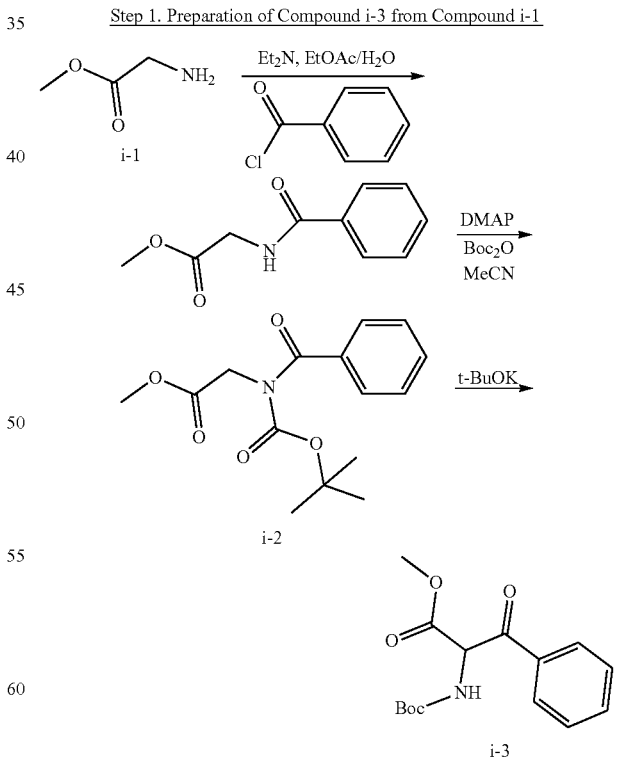

To an inerted 1000 L vessel, water (178 kg) was charged, followed by glycine methyl ester hydrochloride (HCl salt of i-1, 35.0 kg) to form a solution. EtOAc (178 L; 160.6 kg)

was charged and the mixture cooled to 0° C. Triethylamine (56.4 kg; 78 L) was added over about 30 min maintaining internal temperature<10° C. The mixture was cooled to 0° C. and benzoyl chloride (35.6 kg; 29.4 L) added over >30 min maintaining internal temperature<10° C. HPLC analysis at the end of the benzoyl chloride addition showed 100% conversion to benzoylated intermediate.

10% Phosphoric acid (prepared from 9 kg of 85 wt % phosophoric acid and 81 kg H₂O) was then charged over 15 min and the mixture stirred. The lower aqueous layer was removed and then back-extracted with EtOAc twice (178 L; 160.6 kg followed by 89 L; 80.3 kg). Loss to aqueous layer was about 2.1%.

The organic layers were combined and concentrated to ~50 L, then acetonitrile (178 L; 140.0 kg) charged and concentrated to ~50 L. Acetonitrile (178 L; 140.0 kg) was then charged and the solution cooled to 0° C. and DMAP (3.09 kg) charged. Cooling to 0° C. was required to remain below the flash point of MeCN before charging solid via manway.

The mixture was warmed to 20° C. and a solution of Boc anhydride (60.8 kg; 64.7 L) in MeCN (64.7 L; 60.8 kg+10 L rinse) was charged to the mixture over 30 min. The reaction mixture was aged overnight. HPLC analysis showed 100% conversion to Boc-intermediate.

The mixture was degassed via 3×vaccum/N₂ cycles, cooled to 0° C. and a solution of t-BuOK (36.9 kg) in THF (142 L; 126.6 kg) added over 1 h maintaining internal temperature<5° C. The reaction mixture was aged for 1 h at 5-10° C. HPLC analysis showed full conversion to keto-ester.

10% Citric acid (aq.) (prepared from 36.5 kg citric acid and 328.6 kg H₂O) was then added to the mixture, stirred and the lower aqueous layer removed.

5% NaCl (aq.) (prepared from 14.25 kg NaCl and 270.8 kg H₂O) was added to the organics, stirred and the lower aqueous layer removed. The lower brine layer was back-extracted with MTBE (80 kg) and all organics combined.

The combined, washed organics were concentrated to ~300 L, then IPA (178 L; 139.7 kg) added and concentrated down to ~285 L (1H-NMR showed no residual MeCN) then IPA (117 kg) added. The slurry was heated to 50° C. to obtain a solution and H₂O (327.5 kg) added over 1 h maintaining internal temperature at 40-50° C., then cooled to 20° C. over 45 min and aged overnight. Liquor loss was <2% by end of the cool-down.

The slurry was filtered and washed with IPA/H₂O (38.3 kg; 146.3 kg) and the solids dried overnight at 50° C. in vacuo to give ketoester compound i-3 as an off-white solid (65.25 kg; 99.4 LCAP; 100 LCWP) The yield was 89%.

Using the HPLC method described below, the retention time of i-3 was about 4.0 min.

| HPLC Method |
| --- |
| Column: Ascentis Express C18, 100 × 4.6 mm, 2.7 µm particle size; Column Temperature: 40° C.; Flow rate: 1.8 mL/min; Detection: 210 nm, 220 nm, 254 nm; Mobile phase: A: 1.0 ml of 99.9% phosphoric acid (85 w/w %) in 1 L of H₂O B: MeCN |

| Gradient: | | | | | |
| --- | --- | --- | --- | --- | --- |
| Time, min | 0 | 6 | 8 | 9 | 10 |
| A % | 90 | 5 | 5 | 90 | 90 |
| B % | 10 | 95 | 95 | 10 | 10 |

Step 2. Preparation of Compound i-4 from Compound i-3 Through DKR Reduction

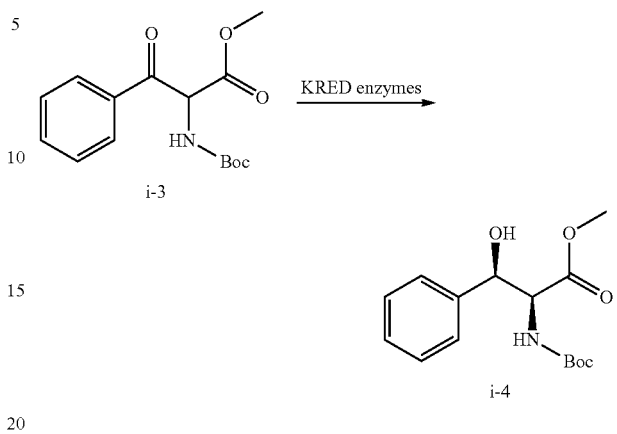

A 0.1M phosphate buffer solution was prepared by dissolving sodium phosphate dibasic dihydrate (8.54 kg) in water (480 kg). The pH was adjusted to 70.0 using HCl (approx 1.5 L).

0.1M phosphate buffer (400 kg) was charged to a 1000 L vessel followed by DMSO (66 kg). D-(+)-glucose (39.2 kg) and NADP disodium salt (0.90 kg) was charged via the manway and the mixture stirred at 30° C. until all solids had dissolved.

The remaining 0.1M phosphate buffer (88.5 kg) was charged to a 400 L vessel, followed by the KRED enzyme of SEQ ID NO. 1 (3.0 kg) and a cofactor recycling system of SEQ ID NO. 3 (0.30 kg). This mixture was stirred slowly at 20° C. until all enzymes had dissolved. Violent stirring should be avoided to prevent form from forming in the mixture. Once dissolved, a hazy yellow solution was obtained.

To a 160 L vessel was charged the keto ester substrate i-3 (32.6 kg) followed by DMSO (66 kg). The mixture was stirred at 30° C. until all the solid had dissolved.

The pH of the glucose/NADP solution was adjusted from 7.19 to 7.50 using 2M sodium hydroxide solution (2.4 kg).

The enzyme solution was then transferred to the 1000 L vessel, followed by a water line wash (5 kg). The pH of the combined solution was then re-adjusted from 7.30 to 7.50 by the addition of 2M sodium hydroxide solution (1.9 kg).

The DMSO solution of the keto ester was then charged to the 1000 L vessel over approximately 4 h, maintaining the temperature in the reaction vessel at 30° C. and maintaining the pH between 7.3 and 7.7.

Starting material crystallized during addition. Reaction mixture was then a slurry throughout. The pH became more acidic as the reaction progressed. The range of 7.3 to 7.7 was maintained by the addition of 2M NaOH.

The reaction was then aged at 30° C., with the pH maintained between 7.3 and 7.7 until reaction was complete. Reaction achieved 90% completion after approximately 5 days. Total uptake of 2M NaOH was 55 kg. Projected total uptake was 60 kg.

The extraction workup was performed in two halves due to vessel volume limitations. The amounts detailed below are for the total batch size.

MTBE (900 L) and methanol (400 L) were charged and the mixture stirred and allowed to settle. A two phase mixture was obtained—upper clear organic layer containing the product and a lower hazy aqueous layer containing all of the enzyme residues. Separation was good but did require a 30-60 min settling time.

The phases were separated and the aqueous extracted with MTBE (300 L). The organic phases were combined and washed with 10% brine (150 L). Total losses to aqueous layers were 1-2% of theory yield.

The organic layer was then concentrated from 1100 L to 95 L by distillation at reduced pressure. Toluene (185 kg) was charged and the batch concentrated to a final volume of 100 L. Batch temperature maintained below 40° C. during distillation.

Total material processed was 64.2 kg. Assay yield was 53.9 kg (86%). Contained ~14% keto ester i-3. ee>99.9%. KF<250 ppm. MTBE not detected by 1H NMR.

Using the HPLC method described below, the retention times of i-3 and i-4 were about 4.5 min and 3.8 min, respectively.

| HPLC Method |
| --- |
| Column: Ascentis Express C18, 100 × 4.6 mm, 2.7 μm particle size; Column Temperature: 40° C.; Flow rate: 1.8 mL/min; Detection: 210 nm; Mobile phase: A: 1.0 ml of 99.9% phosphoric acid (85 w/w %) in 1 L of $H_2O$ B: MeCN |

| Gradient: | | | |
| --- | --- | --- | --- |
| Time, min | 0 | 6 | 8 |
| A % | 90 | 5 | 5 |
| B % | 10 | 95 | 95 |

Step 3. Preparation of Compound i-5 from Compound i-4 through Acetonide Protection

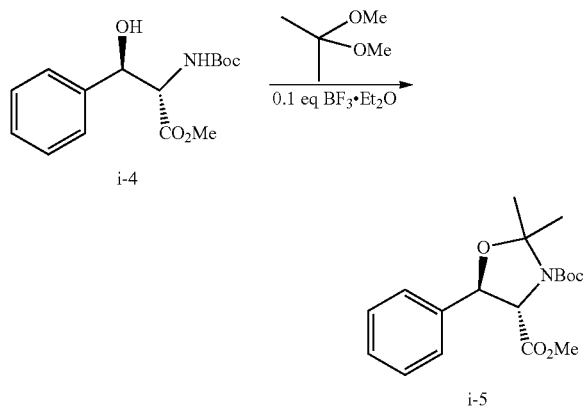

To an inerted 1000 L vessel, the hydroxyester i-4 in toluene (53.9 kg hydroxyester; total solution 114.1 kg) was charged, followed by acetone (257 L; 203 kg) and 2,2-dimethoxypropane (97 L; 82 kg) and the mixture stirred for 5 min. Boron trifluoride diethyl etherate (2.20 L; 2.47 kg) was charged to the mixture over 30 min and aged 15 h overnight at 20° C. (no exotherm was noted). Reaction time was ~ 4 h for completion; HPLC analysis after overnight showed>99% conversion.

Triethylamine (2.4 L; 1.76 kg) was then charged and the mixture concentrated to low volume (~100 L). MTBE (308 L; 229 kg) was charged, followed by 5% $NaHCO_3$ (aq.) (129 L prepared from 6.45 kg $NaHCO_3$ and 122.55 kg $H_2O$) and 10% NaCl (aq.) (129 L prepared from 12.9 kg NaCl 116.1 kg $H_2O$). The mixture was stirred for 5 min, the layers allowed to settle and the lower aqueous layer removed. The washed organics were concentrated to ~75 L, then toluene charged (91 L; 105 kg) and concentrated to ~75 L. Toluene (138 L; 119 kg) was then added. Reaction time was ~4 h for completion; HPLC analysis after overnight showed>99% conversion.

Triethylamine [2.4 L; 1.76 kg] was then charged and the mixture concentrated to low volume, ~100 L. MtBE [308 L; 229 kg] was charged, followed by 5% $NaHCO_3$ (aq.) [129 L prepared from 6.45 kg $NaHCO_3$ and 122.55 kg DI $H_2O$] and 10% NaCl (aq.) [129 L prepared from 12.9 kg NaCl 116.1 kg DI $H_2O$]. The mixture was stirred for 5 min., the layers allowed to settle and the lower aqueous layer removed. The washed organics were concentrated to ~75 L, then toluene charged [91 L; 105 kg] and concentrated to ~75 L. Toluene [138 L; 119 kg] was then added.

Final solution was 176.8 kg and product acetonide i-5 assay was 61.2 kg (100%). Keto ester compound i-3 was still present at 14.2 LCAP.

Using the same HPLC method as in Step 1 of this Example, the retention times of i-4 and i-5 were about 3.2 min and 5.2 min, respectively.

Step 4. Preparation of Compound i-6 Through Borohydride Reduction of Compound i-5

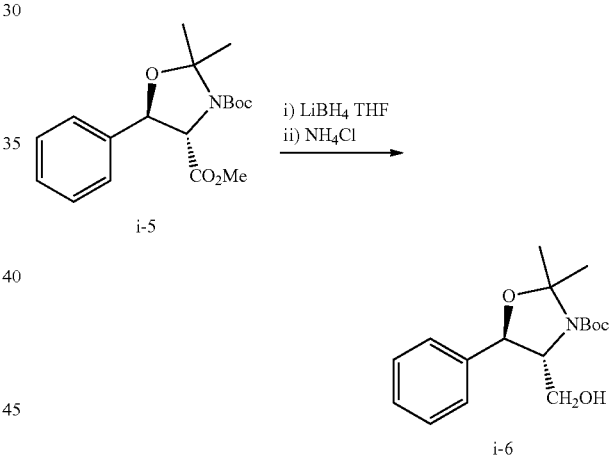

To a 1000 L vessel was charged tetrahydrofuran (218 kg) and 10% lithium borohydride solution in THE (50.8 kg). The mixture was stirred and the temperature adjusted to 20° C.

A solution of acetonide ester i-5 (containing ~14 LCAP keto ester i-3 carried through from the enzymatic DKR step) in toluene (55.9 kg of substrate in a total of 176.8 kg of toluene solution) was charged over 45 min maintaining the batch temperature between 20 and 25° C. The batch was warmed to 35° C. and aged for 18 h. Small exotherm was noted during charging of substrate. Minimal off-gassing was observed. HPLC showed<1% starting material remaining.

The batch was transferred to a 400 L vessel followed by a THE line wash (10 kg). To the 1000 L vessel was charged a solution of ammonium chloride (24.5 kg) in water (245 kg). The ammonium chloride solution was cooled to 0-5° C. and then the batch charged over 90 min, maintaining the temperature between 0 and 5° C. Hydrogen gas evolved. Rate of addition of batch to ammonium chloride quench solution was controlled so as not to pressurise vessel.

The quenched reaction mixture was warmed to 20° C. and stirred for 2 h (until off-gassing ceased). Agitation was stopped and the layers allowed to settle. The lower aqueous phase was run out and the organic washed with ~10% brine (5 kg sodium chloride in 50 kg water). There was some emulsion at interface and so the majority of the organics were removed and the emulsion and aqueous layer re-extracted with toluene (100 kg). The organic phases were combined and concentrated at reduced pressure to 100 L (batch temperature maintained below 40° C.).

Heptane (410 kg) was charged and the mixture warmed to 30° C. The batch was washed with a mixture of acetonitrile (20 kg) in water (300 kg) for 20 min. The aqueous layer was removed and the wash repeated twice more. Washing performed at 30-35° C. to maintain solubility. Diol compound i-16 which has the following structure was reduced from 14 to 2 LCAP:

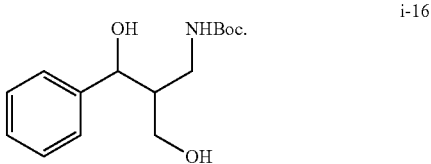 [SMILES: CC(C)(C)OC(=O)NCC(CO)C(O)c1ccccc1]

i-16

The organic phase was then concentrated to 100 L under reduced pressure. Acetonitrile (120 kg) was charged and the batch concentrated to 140 L (142 kg). Assay yield was 55.6 kg (99%) and <2 LCAP of i-16 was present.

Using the same HPLC method as in Step 2 of this Example, the retention times of i-5, i-6 and i-16 diastereomers were about 5.6 min, 4.9 min, 3.0 min and 3.1 min respectively.

Step 5. Preparation of Aldehyde Compound i-7 by TEMPO Oxidation of Compound i-6

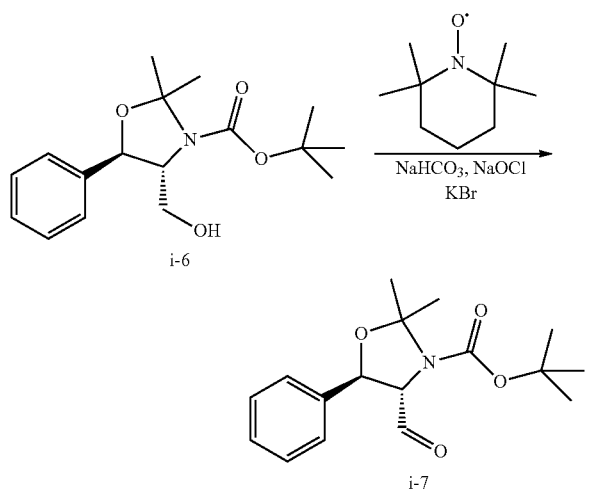

To an inerted 1000 L glass-lined vessel were charged KBr (2.65 kg), NaHCO₃ (4.11 kg) and water (152 kg). The toluene/CH₃CN/heptane solution of the alcohol i-6 (142 kg at 39.2 wt %) was added to the aqueous solution, followed by acetonitrile (83 kg) and toluene (153 kg). The resulting stirred solution was cooled to 0-2° C. Using a diaphragm pump, a solution of TEMPO (0.695 kg) in toluene (2.8 L) was added to the reaction mixture, rinsing the line and pump with toluene (~1 L).

Using an air-driven Teflon-lined pump, sodium hypochlorite (120 kg, 99 L, 13.9 wt % active chlorine) was charged to the vessel through an above-surface addition line. The sodium hypochlorite solution was then added to the reaction mixture over a period of 70 min while maintaining the batch temperature below 10° C. The addition-line was rinsed into the batch with water (1 kg). The batch was aged at <5° C. for 20 min. The sodium hypochlorite does not need to be pre-cooled to 15° C., but should not be at temperatures above ambient (i.e. 23° C.). The addition rate should be maintained within 60-70 min. A longer addition rate will incur larger amounts of both starting material and over-oxidized acid by-product, whilst a shorter run time will probably not be possible due to exothermic activity. The exotherm will cease as soon as addition of the bleach stops. In this case, 4.0 LCAP starting material, 1.3 LCAP acid and 87.4 LCAP aldehyde was obtained. A further 0.05 eq. NaOCl (4 kg) was charged before proceeding with the quench, although the batch was not re-assayed again.

The temperature of the batch was checked at 5° C., and 1 M sodium sulfite (total prepared from 5.04 kg of Na₂SO₃ and 35 kg water; actual amount added was only 18 L of this solution) was then added over a period of 10 min, maintaining the batch temperature below 10° C. The batch temperature was set to 20° C. and aged for 5 min. The batch was tested with starch iodide paper to ensure no oxidant was present.

The bi-phasic mixture was mixed for 10 min and then allowed to settle out. The lower aqueous layer was removed and disposed of. The top organic cut was washed with water (68 kg). The lower aqueous cut as again removed and disposed of. The organic layer was again tested for oxidant with starch iodide paper. (Good hold point-hold solution at 5° C.).

Both cuts were very good and settled fairly quickly. The final organic cut indicated 1.3 LCAP starting material and 91.1 LCAP aldehyde. In both aqueous layers, residual KBr and the acid by-product were removed.

The organic solution was then distilled, under vacuum, to a final volume of ~135 L whilst maintaining temperature<40° C. (~3 volumes based on yield of aldehyde). KF should be <2% water for the subsequent HWE step. In this case the KF was 80 µg/mL.

This afforded a 36.8 wt % solution of aldehyde (131.7 kg total; 36.8 wt %, 48.5 kg assay for i-7; 87% yield (¹H-NMR assay with anisole as internal standard), which was stored in a plastic lined steel drum under nitrogen at 5° C. whilst awaiting further processing. Using the HPLC method described below, the retention times of i-6 and i-7 were about 4.9 min and 5.5 min, respectively.

| HPLC method |
| --- |
| Column: Ascentis Express C18, 100 × 4.6 mm, 2.7 µm particle size; Column Temperature: 40° C.; Flow rate: 1.5 mL/min; Detection: 210 nm, 254 nm; Mobile phase: A: 1.0 ml of 99.9% phosphoric acid (85 w/w %) in 1 L of H₂O B: MeCN |

| Mobile Phase Gradient: | | | | |
| --- | --- | --- | --- | --- |
| Time, min | 0 | 5 | 7.5 | 7.51 |
| A % | 90 | 10 | 10 | 90 |
| B % | 10 | 90 | 90 | 10 |

Step 6. Preparation of i-8 by HWE Coupling of i-7 Aldehyde with Compound a-4

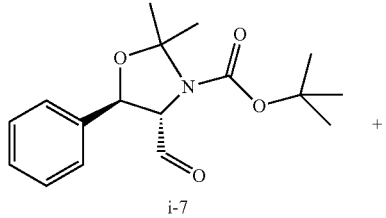

i-7

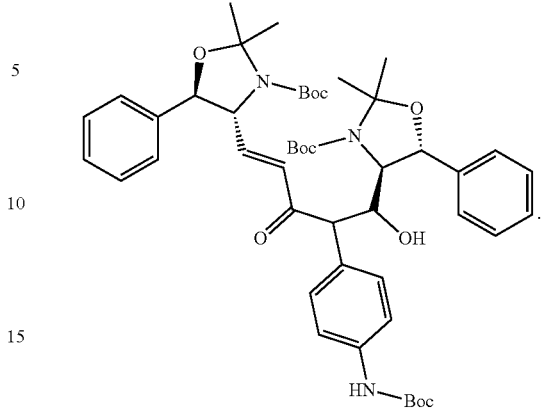

I-21

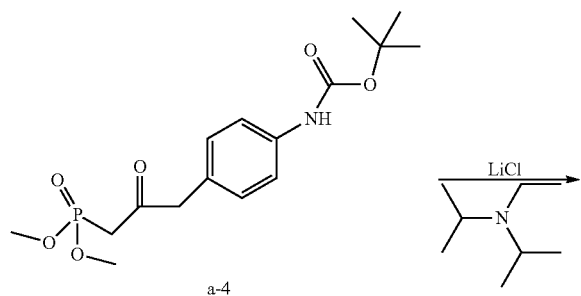

a-4

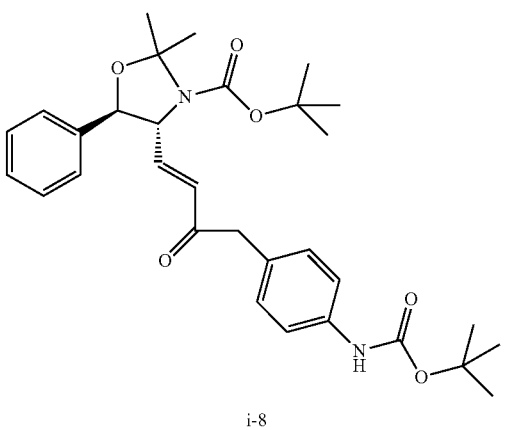

i-8

The phosphonate a-4 (67.4 kg, 1.2 equiv.) and lithium chloride (19.98 kg, 3 equiv.) were charged to a 1000 L vessel, followed by acetonitrile (188.64 kg). The mixture was cooled to ~5° C. and N,N-Diisopropylethylamine (60.95 kg, 3 equiv.) was added while maintaining an internal temperature below 20° C. Once addition was complete the batch was warmed to 40° C. and the solution of aldehyde i-7 in toluene from the previous step was added over 3 h then aged for a further 30 min.

Adding the aldehyde solution to the prepared ylide resulted in a very low level (~1 LCAP) of aldol dimmer by-product I-21 at the end of the reaction:

The batch was cooled to 0° C. and MTBE (177.6 kg) was added followed by citric acid (10% aq.) to adjust the pH to between 6.5 and 7 (6.87 achieved in the plant). If the pH was overshot then addition of 2N NaOH was conveniently used to adjust the pH back into range.

The aqueous lower layer was run off and the organics were washed with 10% sodium bicarbonate solution (240 L), then water (2×120 L). During the first aqueous wash there was some solid in the aqueous layer identified as citric acid salts precipitated due to super saturation. This was conveniently ran off with the aqueous layer.

An assay yield of the final solution showed there was 75.67 kg, 90.1% in the organic stream (Note: this was an estimate based on approximate volume in the vessel) Losses to the aqueous cuts were <0.1%.

The solution was distilled to a minimum volume (~100 L) and iso-propyl alcohol (604.5 kg) was added. The solution was then distilled to a final volume of 616 L (~7 volumes+ product), and the batch was heated to 49° C. Water (46.2 kg, 0.6 volumes) was added and the batch was cooled to 40° C. over 30 min. The batch was seeded and allowed to age for 1 h at 40° C. to establish a seed bed. Water (492.8 kg) was then added to the batch over 1 h whilst marinating the batch temperature at 40° C. The batch was aged for 2 h at 40° C. then cooled to 10° C. over 2 h, and aged at this temperature over night. After the age period an assay of the liquors showed there was a liquor concentration of 2.9 mg/ml. The batch was filtered and the cake was washed with 1:1 of IPA:water (380 L) which had been cooled to 10° C. The solid was dried in vacuo at 40° C. Then co-milled to afford 75.93 kg of the desired product, 100 LCAP, 99 wt %, 89% yield. Losses to the liquors and washes were 3%.

With the success of this protocol the reaction was attempted using only 1.01 equiv of phosphonates a-4, this resulted in a 99% assay yield at the end of reaction.

Using the same IPLC method as in Step 2 of this Example, the retention times of a-4 and i-8 were about 3.8 min and 6.2 min, respectively.

Using procedures similar to Steps 7-9 of Example 1, compound i-11 can be prepared from compound i-8.

While the invention has been described and illustrated with reference to certain particular embodiments thereof, those skilled in the art will appreciate that various changes, modifications and substitutions can be made therein without departing from the spirit and scope of the invention. It is intended, therefore, that the invention be defined by the scope of the claims which follow and that such claims be interpreted as broadly as is reasonable.

What is claimed is:

1. A process for producing compound I-11:

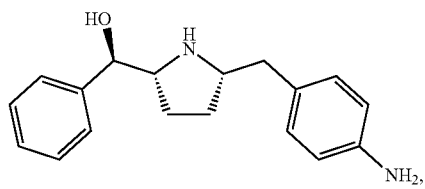

I-11 comprising:

(a) reducing compound I-5:

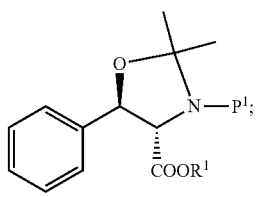

I-5 with a reducing agent at a temperature of 0° C. to 40° C. to produce compound I-6:

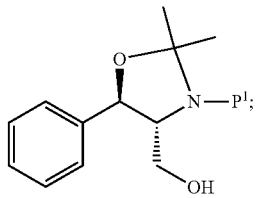

I-6

(b) oxidizing said compound I-6 with an oxidizing agent in the presence of a solvent and a catalyst to produce compound I-7:

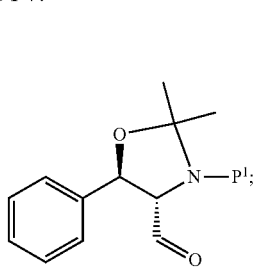

I-7

(c) reacting said compound I-7 with phosphonate compound A-4:

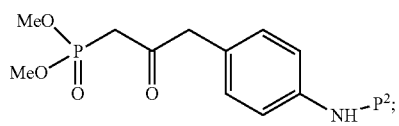

A-4 to produce compound I-8:

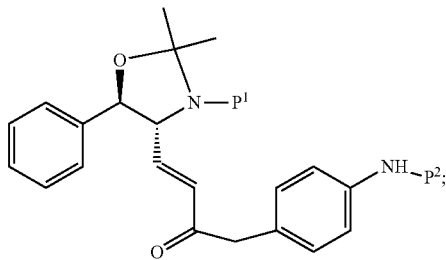

I-8

(d) reducing said compound I-8 in the presence of a catalyst to produce compound I-9:

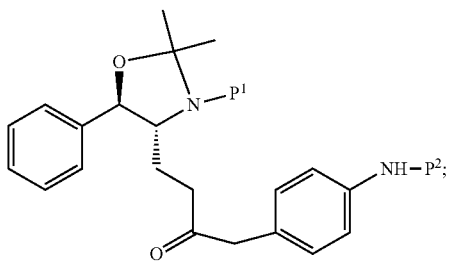

I-9

(e) reacting said compound I-9 with an acid to produce compound I-10:

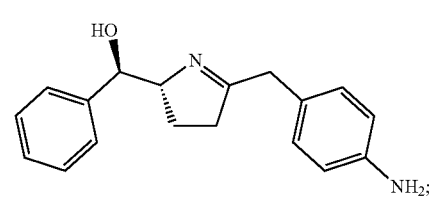

I-10 and (f) reducing said compound I-10 in the presence of a catalyst to produce compound I-11;

wherein said $P^1$ and said $P^2$ are each independently selected from the group consisting of acyl (Ac), benzyl (Bn), t-butyloxycarbonyl (Boc), benzoyl (Bz), carbobenzyloxy (Cbz), 3,4-dimethoxybenzyl (DMPM), 9-fluorenylmethyloxycarbonyl (FMOC), 4-nitrobenzene sulfonyl (Ns), p-methoxybenzyl carbonyl (Moz), and p-toluene sulfonyl (Ts); and said $R^1$ is selected from the group consisting of $C_{1-6}$alkyl, benzyl, and phenyl.

2. The process of claim 1, wherein the reducing agent of step (a) is selected from the group consisting of $LiAlH_4$, $LiBH_4$, $NaBH_4$—LiBr, and DIBAL.

3. The process of claim 1, wherein in step (b) said solvent is selected from the group consisting of tetrahydrofuran (THF), methyl tert-butyl ether (MTBE), dichloromethane ($CH_2Cl_2$), acetonitrile (MeCN), toluene and a mixture comprising two of said foregoing solvents.

4. The process of claim 1, wherein in step (b) said oxidizing agent is selected from the group consisting of sodium hypochlorite (NaOCl), sodium chlorite ($NaClO_2$), hydrogen peroxide, pyridine sulfur trioxide, pyridinium chlorochromate (PCC), and N,N'-dicyclohexycarbodiimide (DCC).

5. The process of claim 1, wherein in step (b) said catalyst is 1-oxyl-2,2,6,6-tetramethylpiperidine (TEMPO) or a TEMPO analogue.

6. The process of claim 1, wherein said reaction between said compound I-7 and said compound A-4 in step (c) is carried out at a temperature of 20 to 40° C. and in the presence of a solvent selected from the group consisting of THF, MTBE, $CH_2Cl_2$, MeCN, toluene and a mixture comprising two of said foregoing solvents.

7. The process of claim 1, wherein said catalyst in step (d) is selected from the group consisting of Pd, Raney Ni, Pt, $PdCl_2$, and $Pd(OH)_2$.

8. The process of claim 1, wherein said reducing in step (d) is carried out in the presence of hydrogen gas.

9. The process of claim 1, wherein said acid in step (e) is selected from the group consisting of HCl, HBr, trifluoroacetic acid (TFA), $MeSO_3H$, TfOH, $H_2SO_4$, para-toluenesulfonic acid, and $RSO_3H$, wherein R is an alkyl, an aryl or a substituted aryl.

10. The process of claim 1, wherein said reducing in step (f) is carried out in the presence of hexamethyldisilazane (HMDS).

11. The process of claim 1, wherein said catalyst in step (f) is selected from the group consisting of Pt on alumina, Pd on alumina, Pd/C, $Pd(OH)_2$—C, Raney Ni, Rh/C, Rh/Al, Pt/C, Ru/C and $PtO_2$.

12. The process of claim 1, wherein $R^1$ is $C_{1-6}$alkyl.

* * * * *

SEQUENCE LISTING

<160> NUMBER OF SEQ ID NOS: 4

<210> SEQ ID NO 1
<211> LENGTH: 249
<212> TYPE: PRT
<213> ORGANISM: Exiguobacterium spp.

<400> SEQUENCE: 1

```
Met Lys Tyr Thr Val Ile Thr Gly Ala Ser Ser Gly Ile Gly Tyr Glu
1               5                   10                  15

Thr Ala Lys Leu Leu Ala Gly Lys Gly Lys Ser Leu Val Leu Val Ala
            20                  25                  30

Arg Arg Thr Ser Glu Leu Glu Lys Leu Arg Asp Glu Val Lys Gln Ile
        35                  40                  45

Ser Pro Asp Ser Asp Val Ile Leu Lys Ser Val Asp Leu Ala Asp Asn
50                  55                  60

Gln Asn Val His Asp Leu Tyr Glu Gly Leu Lys Glu Leu Asp Ile Glu
65                  70                  75                  80

Thr Trp Ile Asn Asn Ala Gly Phe Gly Asp Phe Asp Leu Val Gln Asp
                85                  90                  95

Ile Glu Leu Gly Lys Ile Glu Lys Met Leu Arg Leu Asn Ile Glu Ala
            100                 105                 110

Leu Thr Ile Leu Ser Ser Leu Phe Val Arg Asp His His Asp Ile Glu
        115                 120                 125

Gly Thr Thr Leu Val Asn Ile Ser Ser Ala Gly Gly Tyr Arg Ile Val
130                 135                 140

Pro Asn Ala Val Thr Tyr Cys Ala Thr Lys Phe Tyr Val Ser Ala Tyr
145                 150                 155                 160

Thr Glu Gly Leu Ala Gln Glu Leu Gln Lys Gly Ala Lys Leu Arg
                165                 170                 175

Ala Lys Val Leu Ala Pro Ala Ala Thr Glu Thr Glu Phe Ala Asp Arg
            180                 185                 190

Ser Arg Gly Glu Ala Gly Phe Asp Tyr Ser Lys Asn Val Lys Lys Tyr
        195                 200                 205

His Thr Ala Ala Glu Met Ala Gly Phe Leu His Gln Leu Ile Glu Ser
    210                 215                 220

Asp Ala Ile Val Gly Ile Val Asp Gly Glu Thr Tyr Glu Phe Glu Leu
225                 230                 235                 240

Arg Gly Pro Leu Phe Asn Tyr Ala Gly
                245
```

<210> SEQ ID NO 2
<211> LENGTH: 249
<212> TYPE: PRT
<213> ORGANISM: Artificial Sequence
<220> FEATURE:
<223> OTHER INFORMATION: Engineered variant of ketoreductase from
      Exiguobacterium spp.

<400> SEQUENCE: 2

```
Met Lys Tyr Thr Val Ile Thr Gly Ala Ser Ser Gly Ile Gly Tyr Glu
1               5                   10                  15

Thr Ala Lys Leu Leu Ala Gly Lys Gly Lys Ser Leu Val Leu Val Ala
            20                  25                  30

Arg Arg Thr Ser Glu Leu Glu Lys Leu Arg Asp Glu Val Lys Gln Ile
        35                  40                  45

Ser Pro Asp Ser Asp Val Ile Leu Lys Ser Val Asp Leu Ala Asp Asn
```

```
                    50                  55                  60
Gln Asn Val His Asp Leu Tyr Glu Gly Leu Lys Glu Leu Asp Ile Glu
 65                  70                  75                  80

Thr Leu Ile Asn Asn Ala Gly Phe Gly Asp Phe Asp Leu Val Gln Asp
                 85                  90                  95

Ile Glu Leu Gly Lys Ile Glu Lys Met Leu Arg Leu Asn Ile Glu Ala
            100                 105                 110

Leu Thr Ile Leu Ser Ser Leu Phe Ala Arg Asp His His Asp Ile Glu
            115                 120                 125

Gly Thr Thr Leu Val Asn Ile Ser Ser Leu Gly Gly Tyr Arg Ile Val
        130                 135                 140

Pro Asn Ala Val Thr Tyr Cys Ala Thr Lys Phe Tyr Val Ser Ala Tyr
145                 150                 155                 160

Thr Glu Gly Leu Ala Gln Glu Leu Gln Lys Gly Gly Ala Lys Leu Arg
                165                 170                 175

Ala Lys Val Leu Ala Pro Ala Thr Glu Thr Glu Phe Val Asp Arg
            180                 185                 190

Ala Arg Gly Glu Ala Gly Phe Asp Tyr Ser Lys Asn Val His Lys Tyr
        195                 200                 205

His Thr Ala Ala Glu Met Ala Gly Phe Leu His Gln Leu Ile Glu Ser
    210                 215                 220

Asp Ala Ile Val Gly Ile Val Asp Gly Glu Thr Tyr Glu Phe Glu Leu
225                 230                 235                 240

Arg Gly Pro Leu Phe Asn Tyr Ala Gly
                245
```

<210> SEQ ID NO 3
<211> LENGTH: 261
<212> TYPE: PRT
<213> ORGANISM: Artificial Sequence
<220> FEATURE:
<223> OTHER INFORMATION: Engineered variant of glucose dehydrogenase
    from Bacillus subtilis.

<400> SEQUENCE: 3

```
Met Tyr Pro Asp Leu Lys Gly Lys Val Val Ala Ile Thr Gly Ala Ala
  1               5                  10                  15

Ser Gly Leu Gly Lys Ala Met Ala Ile Arg Phe Gly Lys Glu Gln Ala
             20                  25                  30

Lys Val Val Ile Asn Tyr Tyr Ser Asn Lys Gln Asp Pro Asn Glu Val
         35                  40                  45

Lys Glu Glu Val Ile Lys Ala Gly Gly Glu Ala Val Val Val Gln Gly
     50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160
```

-continued

Ser Lys Gly Gly Met Lys Leu Met Thr Glu Thr Leu Ala Leu Glu Tyr
            165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
            245                 250                 255

Gln Ala Gly Arg Gly
            260

<210> SEQ ID NO 4
<211> LENGTH: 261
<212> TYPE: PRT
<213> ORGANISM: Artificial Sequence
<220> FEATURE:
<223> OTHER INFORMATION: Engineered variant of glucose dehydrogenase
      from Bacillus subtilis.

<400> SEQUENCE: 4

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
            85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Met Lys Leu Met Thr Lys Thr Leu Ala Leu Glu Tyr
            165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Lys Glu Ala Ser Tyr Val Thr
225                 230                 235                 240

```
Gly Ile Thr Leu Phe Ala Asp Gly Gly Met Thr Leu Tyr Pro Ser Phe
            245                 250                 255
Gln Ala Gly Arg Gly
        260
```